US012746408B2

(12) United States Patent
Estrela Arigüel et al.

(10) Patent No.: US 12,746,408 B2
(45) Date of Patent: Sep. 29, 2026

(54) NON-INVASIVE CANCER TREATMENT

(71) Applicants: SCIENTIA BIOTECH S.L, Valencia (ES); UNIVERSITAT DE VALÈNCIA, Valencia (ES)

(72) Inventors: José María Estrela Arigüel, Valencia (ES); José Juan Herrera Gaspar, Valencia (ES); Rosa María Cibrian Ortiz De Anda, Valencia (ES); Enrique Navarro Camba, Valencia (ES); María Elena Obrador Pla, Valencia (ES)

(73) Assignees: SCIENTIA BIOTECH S.L, Valencia (ES); UNIVERSITAT DE VALENCIA, Valencia (ES)

( * ) Notice: Subject to any disclaimer, the term of this patent is extended or adjusted under 35 U.S.C. 154(b) by 588 days.

(21) Appl. No.: 18/546,214

(22) PCT Filed: Feb. 11, 2022

(86) PCT No.: PCT/EP2022/053424
§ 371 (c)(1),
(2) Date: Aug. 11, 2023

(87) PCT Pub. No.: WO2022/171826
PCT Pub. Date: Aug. 18, 2022

(65) Prior Publication Data

US 2024/0131352 A1 Apr. 25, 2024

(30) Foreign Application Priority Data

Feb. 12, 2021 (EP) .................................... 21382115

(51) Int. Cl.
*A61N 7/02* (2006.01)
*A61F 7/02* (2006.01)
(Continued)

(52) U.S. Cl.
CPC ................ *A61N 2/002* (2013.01); *A61F 7/02* (2013.01); *A61N 2/004* (2013.01); *A61N 2/02* (2013.01);
(Continued)

(58) Field of Classification Search
CPC .......... A61N 2/002; A61N 2/004; A61N 2/02; A61N 7/02; A61N 2007/0004;
(Continued)

(56) References Cited

U.S. PATENT DOCUMENTS 4,934,365 A 6/1990 Morgenthaler
5,183,456 A * 2/1993 Liboff ...................... A61N 2/02 600/15
(Continued)

FOREIGN PATENT DOCUMENTS

CA 2738073 C * 4/2016 ............... A61N 5/10
CN 102488967 A 6/2012
(Continued)

OTHER PUBLICATIONS

Estrela et al., "Elimination of Ehrlich tumours by ATP-induced growth inhibition, glutathione depletion and X-rays," *Nature Medicine 1*(1):84-88, Jan. 1, 1995. (5 pages).
(Continued)

*Primary Examiner* — Brian L Casler
(74) *Attorney, Agent, or Firm* — Seed Intellectual Property Law Group LLP

(57) ABSTRACT

An apparatus (1) for treating a cancerous target site is provided. The apparatus comprises an electromagnetic emitter (10) comprising one or more electrodes with an electrically insulating coating for preventing electrical contact between the electrodes and the target site. The electromagnetic emitter (10) is configured to provide a tumour treating field at a target site (30) via the one or more electrodes, the
(Continued)

tumour treating field being non-ionizing alternating electromagnetic field having a frequency of between 10 kHz to 300 kHz; and further having a magnetic flux density of between 0.1 pT and 1 mT. The apparatus further comprises a heat source (20) configured to provide heating at the target site to cause hyperthermia at the target site. The apparatus is configured to apply the non-ionizing alternating electromagnetic field and the heating independently. The apparatus comprises an electronic controller for electronically controlling the electromagnetic emitter and the heat source.

16 Claims, 16 Drawing Sheets

(51) Int. Cl.

| | |
|---|---|
| ***A61N 2/00*** | (2006.01) |
| ***A61N 2/02*** | (2006.01) |
| *A61F 7/00* | (2006.01) |
| *A61N 7/00* | (2006.01) |

(52) U.S. Cl.

CPC ........ *A61N 7/02* (2013.01); *A61F 2007/0054* (2013.01); *A61F 2007/0282* (2013.01); *A61N 2007/0004* (2013.01)

(58) Field of Classification Search

CPC .......... A61N 1/0492; A61N 2007/0078; A61N 1/403; A61N 5/0625; A61N 2007/0095; A61N 2007/025; A61N 2007/027; A61N 1/36002; A61F 7/02; A61F 2007/0054; A61F 2007/0282

USPC ............................................................ 600/13

See application file for complete search history.

(56) References Cited

U.S. PATENT DOCUMENTS

| | | | | |
|---|---|---|---|---|
| 5,734,033 | A | 3/1998 | Reed | |
| 5,831,066 | A | 11/1998 | Reed | |
| 6,565,887 | B1 | 5/2003 | Gray et al. | |
| 6,640,139 | B1 | 10/2003 | Ueberle | |
| 7,410,469 | B1 * | 8/2008 | Talish | A61N 7/00 600/15 |
| 10,881,882 | B1 | 1/2021 | Schwarz et al. | |
| 2004/0199070 | A1 | 10/2004 | Krockel | |
| 2011/0306870 | A1 | 12/2011 | Kuhn | |
| 2012/0253099 | A1 | 10/2012 | Mon et al. | |
| 2013/0053620 | A1 | 2/2013 | Susedik et al. | |
| 2013/0238061 | A1 | 9/2013 | Ron Edoute et al. | |
| 2014/0276743 | A1 | 9/2014 | Curley | |
| 2017/0014637 | A1 | 1/2017 | Basser | |
| 2017/0165003 | A1 | 6/2017 | Schoenbach et al. | |
| 2018/0001105 | A1 * | 1/2018 | Botsford | A61N 2/02 |
| 2020/0107882 | A1 | 4/2020 | Townley et al. | |
| 2020/0246179 | A1 | 8/2020 | Peyman | |
| 2020/0254272 | A1 | 8/2020 | Sharma | |
| 2020/0306554 | A1 | 10/2020 | Ron Edoute et al. | |
| 2021/0401288 | A1 * | 12/2021 | Weil | A61B 5/0064 |

FOREIGN PATENT DOCUMENTS

| | | | | |
|---|---|---|---|---|
| CN | 103272332 | A * | 9/2013 | |
| CN | 106794354 | A | 5/2017 | |
| CN | 109475735 | A | 3/2019 | |
| CN | 111481823 | A | 8/2020 | |
| WO | WO 9837907 | A1 | 9/1998 | |
| WO | WO-0156656 | A1 * | 8/2001 | A61N 1/40 |
| WO | WO 03040182 | A1 | 5/2003 | |
| WO | WO 2020141527 | A1 | 7/2020 | |

OTHER PUBLICATIONS

Gumireddy et al., "NOV-002, A Glutathione Disulfide Mimetic, Suppresses Tumor Cell Invasion and Metastasis," *Journal of Carcinogenesis & Mutagenesis S7*, Apr. 30, 2013. (6 pages).

Kawamura et al., "A small molecule that induces reactive oxygen species via cellular glutathione depletion," *Biochemical Journal 463*:53-63, Jul. 11, 2014. (13 pages).

McBean et al., "Molecular mechanisms of cystine transport," *Biochemical Society Transactions 29*(Part 6):717-722, Nov. 2001. (6 pages).

Mena et al., "Bcl-2 and Glutathione Depletion Sensitizes B16 Melanoma to Combination Therapy and Eliminates Metastatic Disease," *Clinical Cancer Research 13*(9):2658-2666, May 1, 2007. (9 pages).

Min et al., "Glucocorticoid receptor antagonist sensitizes TRAIL-induced apoptosis in renal carcinoma cells through up-regulation of DR5 and down-regulation of c-FLIP(L) and Bcl-2," *Journal of Molecular Medicine 90*:309-319, Oct. 19, 2011. (11 pages).

Obrador et al., "γ-Glutamyl Transpeptidase Overexpression Increases Metastatic Growth of B16 Melanoma Cells in the Mouse Liver," *Hepatology 35*(2):74-81, Jan. 2002. (8 pages).

Obrador et al., "Intertissue Flow of Glutathione (GSH) as a Tumor Growth-promoting Mechanism," *The Journal of Biological Chemistry 286*(18):15716-15727, May 6, 2011. (12 pages).

Olson et al., "Detection of MRP Functional Activity: Calcein AM but not BCECF AM as a Multidrug Resistance-Related Protein (MRP1) Substrate," *Cytometry 46*:105-113, Apr. 15, 2001. (9 pages).

Ortega et al., "Glutathione in Cancer Cell Death," *Cancers 3*:1285-1310, Mar. 11, 2011. (26 pages).

Pei et al., "Targeting Aberrant Glutathione Metabolism to Eradicate Human Acute Myelogenous Leukemia Cells," *The Journal of Biological Chemistry 288*(47):33542-33558, Nov. 22, 2013. (17 pages).

Shao et al., "BET Protein Inhibitor JQ1 Attenuates Myc-Amplified MCC Tumor Growth In Vivo," *Cancer Research 74*(23):7090-7102, Dec. 1, 2014. (13 pages).

Silber et al., "Adaptation of γ-Glutamyl Transpeptidase Assay to Microtiter Plates," *Analytical Biochemistry 158*:68-71, Oct. 1986. (4 pages).

Terradez et al., "Depletion of tumour glutathione in vivo by buthionine sulphoximine: modulation by the rate of cellular proliferation and inhibition of cancer growth," *Biochemical Journal 292*:477-483, Jun. 1, 1993. (7 pages).

Trachootham et al., "Selective killing of oncogenically transformed cells through a ROS-mediated mechanism by β-phenylethyl isothiocyanate," *Cancer Cell 10*:241-252, Sep. 11, 2006. (12 pages).

* cited by examiner

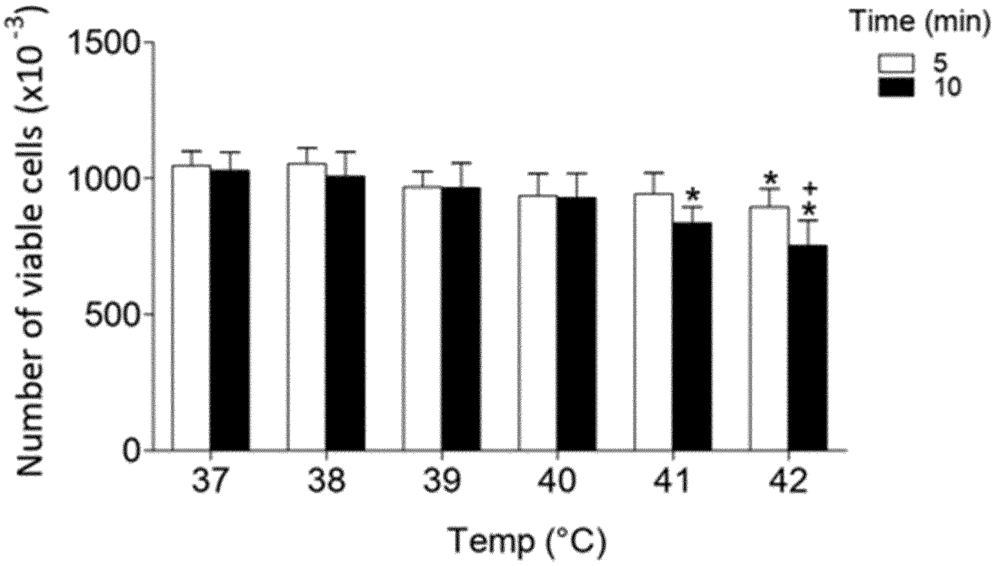
FIG. 14
FIG. 15A FIG. 15B FIG. 15C
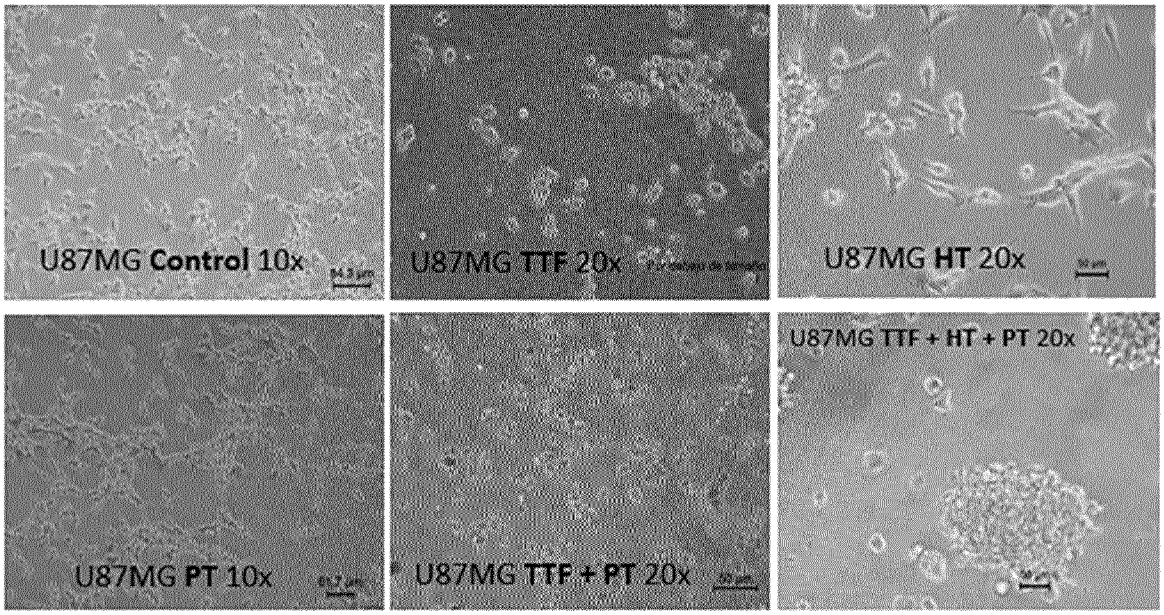
FIG. 15D FIG. 15E FIG. 15F FIG. 21A
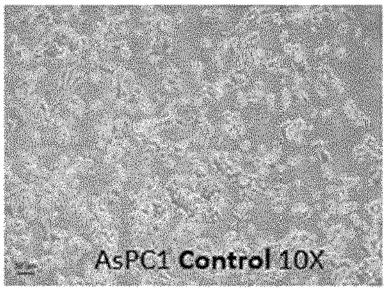
FIG. 21B
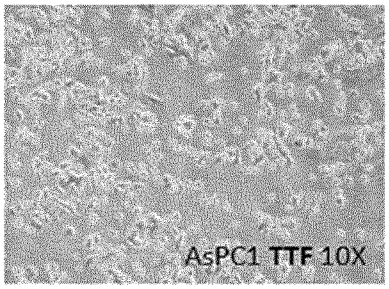
FIG. 21C
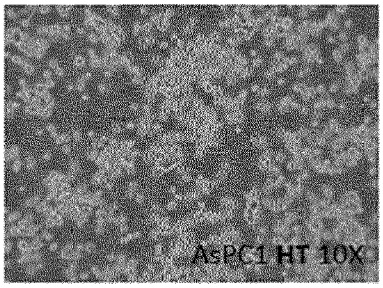
FIG. 21D
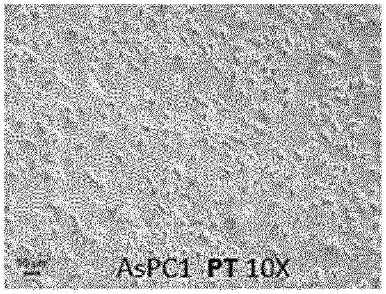
FIG. 21E
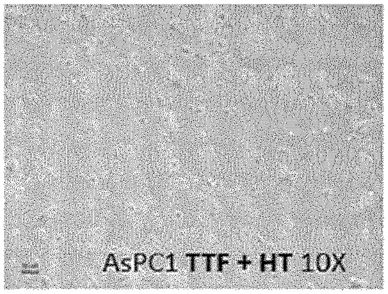
FIG. 21F
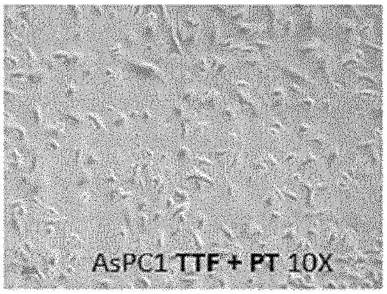
FIG. 21G
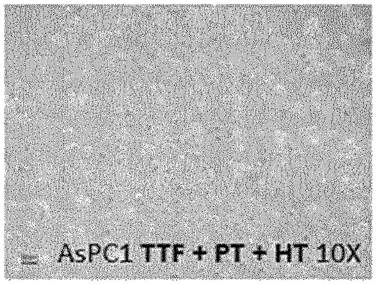
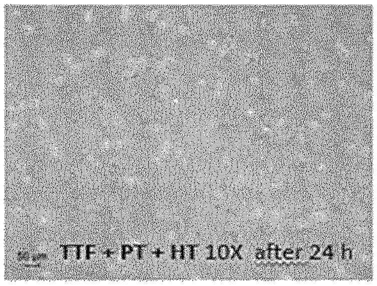
FIG. 21H FIG. 26A
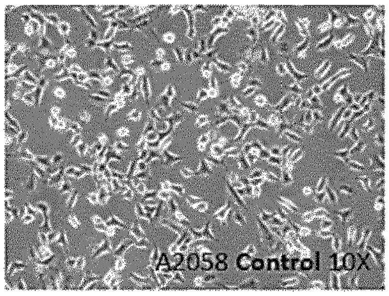
FIG. 26B
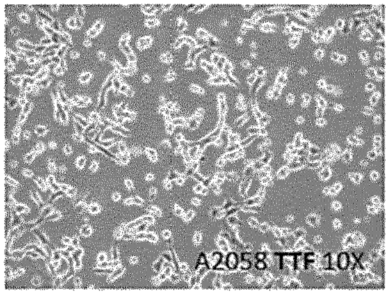
FIG. 26C
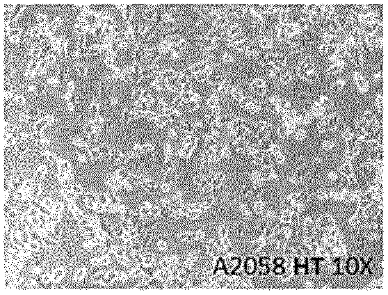
FIG. 26D
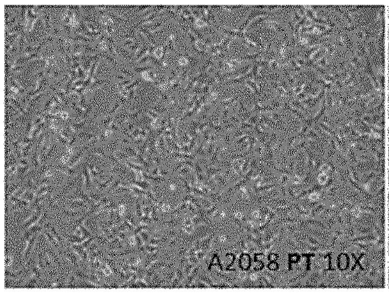
FIG. 26E
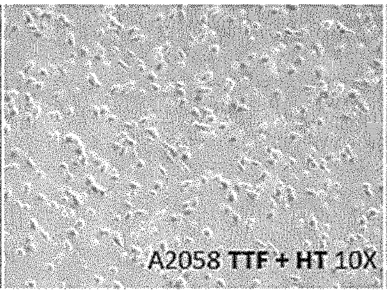
FIG. 26F
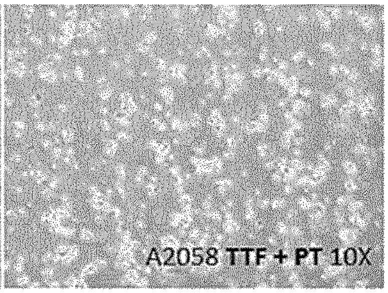
FIG. 26G
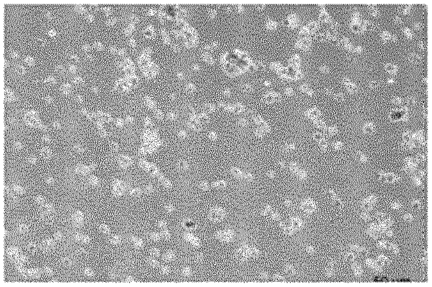
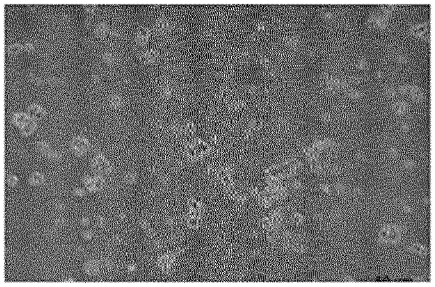
FIG. 26H

NON-INVASIVE CANCER TREATMENT

TECHNICAL FIELD

The present disclosure relates to an apparatus for treating a cancerous target site. More specifically, the present disclosure relates to an apparatus configured to provide a non-ionizing alternating electromagnetic field and local heating at the target site. The disclosure also relates to associated methods for treating a cancerous site and compositions for use in treating a cancerous target site.

BACKGROUND

Non-invasive methods of treating cancer are important methods, particularly for cancers such as glioblastoma which are difficult to remove by surgery. There is a desire for new non-invasive methods of treating cancer which effectively reduce or eliminate the cancerous cells from a target site in the body.

Radiotherapy is a type of cancer therapy which uses ionizing radiation to kill malignant cells at a target site. The ionizing radiation is provided to the target site, which causes damage by the direct or indirect action of radiation on DNA and other cell molecules. In the direct action, the radiation hits e.g. the DNA molecule directly, disrupting its molecular structure. Such structural change leads to cell damage or even cell death, and thus provides a mechanism for treatment of malignant cells.

Another form of treatment, known as alternating electric field therapy or tumour treating fields (TT-Fields) applies non-ionizing electric fields to the target site. The mechanism of TT-Fields which renders it useful for cancer treatment is different to that of radiotherapy. In particular, during the formation of mitotic spindles, the microtubule assembly deforms. Mitosis of tumour cells remains in the interdivision stage for a long time. When the cleavage furrow forms in mid to late mitosis, all polar molecules and dipoles in cells undergo di-electrophoresis under the action of TT-Fields, which accumulates in the cleavage furrow and eventually causes the cell membrane to rupture. Mitotic outcomes elicited by TT-Fields application include abnormal chromosome segregation, which triggers different forms of cell death.

Hyperthermia is a known method for treating a cancerous site. However, it can be difficult to target the cancerous site effectively. On the one hand, tissue surrounding the area being treated may also be affected by hyperthermia, particularly when the cancerous site is heated to a high temperature. On the other hand, the cancerous site may not be effectively destroyed if the site is not heated to a sufficiently high temperature. Further, whilst applying heat to a cancerous site may cause cell damage and even cell death at the cancerous site, if the heat is not correctly and accurately applied to the cancerous site in the correct dose, the cancerous site may be resistant to such heating. For example, if the hyperthermia heats up the healthy surrounding tissue in addition to the cancerous growth, blood flow will be enhanced, and nutrients supply to the cancerous growth may be higher. Thus, under some circumstances the high blood flow as a result of heating helps the dissemination of nutrients which could reach the cancerous site and therefore have the opposite intended effect, or at least result in an ineffective treatment. Further, different phases in the cell cycle of cancerous cells have been observed to have different resistances to heating. Yet further, temperature elevations in cells transiently upregulate heat shock genes that encode a class of heat shock proteins (HSPs). The mechanism responsible for the heat shock response is an autoregulatory loop; HSPs normally keep the responsible transcription factor (HSF-1) inactive but upon heating HSP bind with higher affinity to unfolded proteins, triggering the release of HSF-1 from HSP which initiates HSP gene transcription. Once the protein damage/aggregation is restored after the heat shock by the HSP, substrate-free HSP themselves may be involved in attenuating the response by rebinding HSF-1. As a result, HSP levels transiently rise after heating but also gradually decline again upon prolonged stress-free periods. The upregulation of HSP is closely associated with a transient resistant state of cells towards a subsequent second heat shock. It is thought that the elevated HSP levels, by their chaperone activity, protect cells against protein damage induced by further heating. Accordingly, there is a need to provide hyperthermia which provides the required heating to the cancerous site more accurately and reliably, in order to avoid any resistance to heating of the cancerous cells as a result of deviation from the required amount of applied heat.

Many methods of hyperthermia require a mediator (such as a nanoparticle fluid) to be administered to the site. The mediator is then heated, for example by an electric field, which then indirectly heats the target site. The mediator may be heated using an electric field which has the same or similar frequency range as TT-fields. This may be seen as advantageous as the cancerous site is attacked both via hyperthermia and via the TT-field mechanism. However, as the mediator is a fluid injected into the patient's body, the location of heating when the electromagnetic radiation is administered is hard to control.

There is a desire to find more effective cancer treatment methods for the above methods of treatment.

BRIEF DESCRIPTION OF THE INVENTION

The present invention confronts the problem of providing more effective cancer treatment methods by providing an apparatus for treating a cancerous target site, comprising:

- a electromagnetic emitter configured to provide a non-ionizing alternating electromagnetic field at a target site; and
- a heat source configured to provide heating at the target site to cause hyperthermia at the target site;

wherein the apparatus is configured to apply the non-ionizing alternating electromagnetic field and the heating independently. In particular, the heat source is configured to provide direct heating at the target site.

It is herein noted that the heat source may be any heat source which heats a specific target site without the use of a mediator (e.g. directly and not indirectly via a mediator).

In a preferred embodiment, the apparatus is configured to provide the non-ionizing alternating electromagnetic field at the target for a first time period, and to provide the direct heating at the target site for a second time period. The second time period may partially or fully overlap with the first time period. For example, the first time period may begin at the same time as the second time period, or may begin a predetermined amount of time after the first time period begins, or may begin when the first time period expires. It is preferred that the first and second time periods completely overlap so that the TT-Fields and heating are applied to the site simultaneously, providing a synergistic effect on the cells in the target site as discussed in further detail below.

It is noted that the sequence of the first and second time periods may be repeated two or more times. For example, the apparatus may be configured to apply the non-ionizing alternating electromagnetic field for a first time period, and apply the heating for a second time period a predetermined time after the first period begins. Subsequently, the apparatus may be configured to, again, apply the non-ionizing alternating electromagnetic field for a first time period, and apply the heating for a second time period the predetermined time after the first period begins. The length of the first and second time periods, and their start times relative to each other, may be configurable by a user or according to one or more schedules saved in a memory of the apparatus.

Preferably, the apparatus is configured to provide the non-ionizing alternating electromagnetic field at the target site for a first time period of between 1 minute and 24 hours.

In another preferred embodiment, the apparatus is further configured to provide the heating at the target site for a second time period of between 1 minute and 360 minutes. The heating may be applied simultaneously to the non-ionizing alternating electromagnetic field for a third time period. The third time period may be all or part of the second time period.

In another preferred embodiment, the electromagnetic emitter is configured to provide an alternating electromagnetic field having a frequency of between 10 kHz to 500 kHz and more preferably between 10 kHz and 300 kHz, and even more preferably 100 kHz to 300 kHz. It is observed that the therapeutic effect of the tumour-treating field is significantly increased when the frequency is below 300 kHz.

In another preferred embodiment, the electromagnetic emitter is configured to provide an alternating electromagnetic field at the target site having a magnetic flux density of between 0.1 pT and 1 mT, or between 0.1 pT and 100 μT, or between 100 μT and 1 mT and/or an electric field strength of between 1 V/cm and 3 V/cm.

In another preferred embodiment, electromagnetic emitter is configured to provide an alternating electromagnetic field at the target site having a magnetic flux density of between 0.5 μT and 1 mT, and more preferably between 8 μT and 1 mT.

In another preferred embodiment, the heat source is configured to heat the target site to a temperature of at least 42° C. and preferably between 42° C. and 57° C. Heating the target site to a temperature of at least 42° C. induces heating effects on the target site which corresponds to extreme hyperpyrexia.

In another preferred embodiment, the heat source comprises an ultrasonic emitter configured to provide ultrasound radiation to the target site, optionally wherein the ultrasound radiation has one or more focal areas in the target site. The one or more focal areas may be provided from a single transducer or a plurality of transducers.

In a further preferred embodiment, the heat source comprises one or more of:

- an electromagnetic emitter configured to provide electromagnetic radiation to the target site;
- a fluidic pump configured to pump fluid to the target site and a heater to heat the fluid before it reaches the target site; and/or
- a conductive heat emitter configured to provide heat to the target site by conduction of heat.

In a still further preferred embodiment, the apparatus additionally comprises an electronic controller for electronically controlling the electromagnetic emitter and the heat source.

A further aspect of the present invention refers to a method for treating a cancerous target site using an apparatus according to the supra embodiments, wherein the apparatus may take any configuration disclosed therein and wherein the method is preferably implemented by suitably positioning the emitter 10 and heat source 20 on the patient. For example, the applicators of the electromagnetic emitter 10 may be placed at predetermined points on the patient's body and the heat source 20 (for example the transducer 204 described in relation to FIG. 2) may also be suitably positioned. Wherein the method comprises:

In step S1, the non-ionizing alternating electromagnetic field is provided to give a magnetic flux density at the target site using electromagnetic emitter 10.

In step S2, the heat (and more particularly direct heat) is provided to the target site using heat source 20. This may be provided whilst the electromagnetic field is also being provided to the target site 30 or within a predetermined time before or after the electromagnetic field is provided. In some embodiments, it may be that only the alternating electromagnetic field is provided to produce the magnetic flux density at the target site without the heating for a first time period, before both are provided simultaneously to the target site.

Optionally, in step S3, an anti-carcinogenic composition is provided to the target site. The anti-carcinogenic composition may be administered by any suitable means, such as orally or intravenously. It is noted that the anti-carcinogenic composition may be provided before or simultaneously to steps S1, S2 and step S4 or a predetermined time after step S1, S2 or S4.

Examples of anti-carcinogenic compositions that may be used to implement the present invention are described in detail throughout the present invention.

Also optionally, in step S4, a Glutathione (GSH) depleting composition is provided to the target site in addition to the anti-carcinogenic compound. The GSH depleting composition may be administered by any suitable means, such as orally or intravenously. It is noted that the GSH depleting composition may be provided before or simultaneously to steps S1, S2 and step S3 or a predetermined time after step S1, S2 or S3, preferably at a predetermined time after step S3. Examples of GSH depleting compositions that may be used to implement the present invention are described in detail throughout the present invention.

In step S5, the direct heating is stopped and in step S6 the non-ionizing alternating electric field is stopped. It is noted that steps S5 and S6 may occur simultaneously or the direct heating may be stopped before the non-ionizing alternating electromagnetic field is stopped, such that only the non-ionizing alternating electromagnetic field is applied for a predetermined time after the direct heating is stopped.

A still aspect of the present invention, refers to an anti-carcinogenic composition for use in a method for treating a cancerous target site using an apparatus according to the supra embodiments, wherein the apparatus may take any configuration disclosed therein and wherein the method is preferably implemented by suitably positioning the emitter 10 and heat source 20 on the patient. For example, the applicators of the electromagnetic emitter 10 may be placed at predetermined points on the patient's body and the heat source 20 (for example the transducer 204) may also be suitably positioned. Wherein the method comprises:

In step S1, the non-ionizing alternating electromagnetic field is provided to give a magnetic flux density at the target site using electromagnetic emitter 10.

In step S2, the heat (and more particularly direct heat) is provided to the target site using heat source 20. This may be provided whilst the electromagnetic field is also being provided to the target site 30 or within a predetermined time before or after the electromagnetic field is provided. In some embodiments, it may be that only the alternating electromagnetic field is provided to produce the magnetic flux density at the target site without the heating for a first time period, before both are provided simultaneously to the target site.

In step S3, an anti-carcinogenic composition is provided to the target site. The anti-carcinogenic composition may be administered by any suitable means, such as orally or intravenously. It is noted that the anti-carcinogenic composition may be provided before or simultaneously to steps S1, S2 and step S4 or a predetermined time after step S1, S2 or S4. Examples of anti-carcinogenic compositions that may be used to implement the present invention are described in detail through out the present invention.

Optionally, in step S4, a Glutathione (GSH) depleting composition is provided to the target site in addition to the anti-carcinogenic compound. The GSH depleting composition may be administered by any suitable means, such as orally or intravenously. It is noted that the GSH depleting composition may be provided before or simultaneously to steps S1, S2 and step S3 or a predetermined time after step S1, S2 or S3, preferably at a predetermined time after step S3.

Examples of GSH depleting compositions that may be used to implement the present invention are described in detail through out the present invention.

In step S5, the direct heating is stopped and in step S6 the non-ionizing alternating electric field is stopped. It is noted that steps S5 and S6 may occur simultaneously or the direct heating may be stopped before the non-ionizing alternating electromagnetic field is stopped, such that only the non-ionizing alternating electromagnetic field is applied for a predetermined time after the direct heating is stopped.

BRIEF DESCRIPTION OF THE DRAWINGS

Embodiments will now be explained in detail, by way of non-limiting example only, with reference to the accompanying figures described below.

FIG. 14 shows in vitro experimental data for the effect on cell viability for U87MG cells when exposed to heat;

FIGS. 15A-F how microscopic images of in vitro U87MG cell cultures after exposed to different external treatments, and a control image;

FIGS. 21A to 21H show microscopic images of in vitro AsPC1 cell cultures after exposed to different external treatments, and a control image;

FIGS. 26A to 26H show microscopic images of in vitro A2058 cell cultures after exposed to different external treatment, and a control image.

DETAILED DESCRIPTION

The present invention related to an apparatus which is configured to provide both a non-ionizing alternating electromagnetic field and hyperthermia to a target site, wherein the electromagnetic field and hyperthermia can be provided independently. The electromagnetic field may be applied, for example, by means of a magnetic applicator that provides a magnetic flux density in the target site. In hyperthermia treatments involving a mediator, such an alternating electromagnetic field is provided which also may be absorbed by the mediator. However, as the mediator absorbs the electromagnetic energy, the tumour-treating effects of the electromagnetic field may be reduced. The present invention overcomes this problem by providing hyperthermia independently such that both treatments can be provided to the cancerous site without reducing the effectiveness of the other. In the present invention, the tumour-treating effects are due to a combined application of electromagnetic fields with direct hyperthermia. The electromagnetic field may be introduced with a magnetic field applicator. In some further examples of the present disclosure, the treatment may further include the administration of an anti-cancer composition.

As used herein, the term "tumour treating field", "TT-Field" or "TTF" may be understood to mean an oscillating electromagnetic field applied to a target site. In particular, the electromagnetic field is generated by applicators which are electrically isolated from the target site so that electrical current does not flow between the target site and the applicators.

Figure 1:
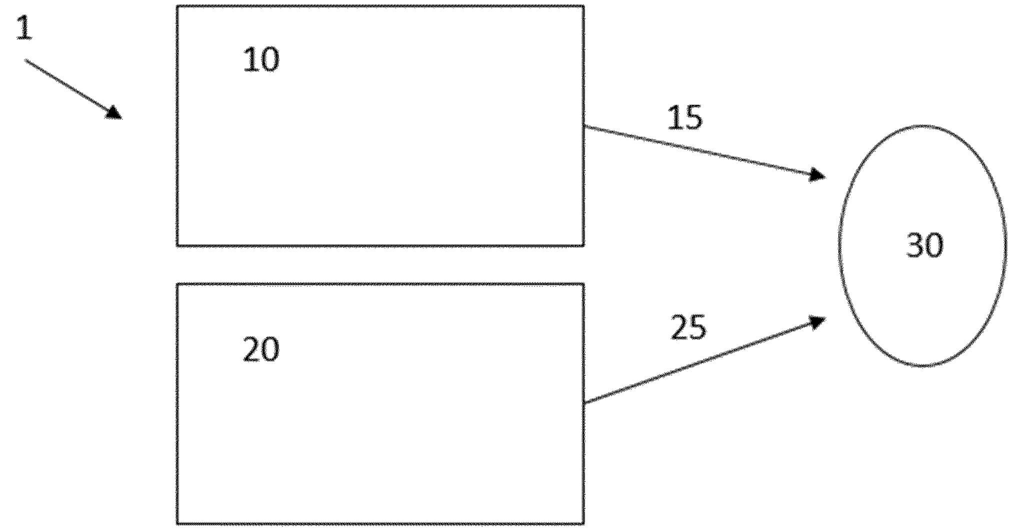
FIG. 1 shows a schematic diagram of an apparatus for treating a cancerous target site according to one or more embodiments.

FIG. 1 shows a schematic diagram of an apparatus 1 for treating a cancerous target site 30. The apparatus comprises an electromagnetic emitter 10 and a heat source 20. The electromagnetic emitter 10 is configured to provide a non-ionizing alternating electromagnetic field 15 at the target site 30. The heat source 20 is configured to provide direct heating 25 at the target site 30 to cause hyperthermia at the target site 30. In one configuration, the apparatus 1 is configured to provide the non-ionizing alternating electromagnetic field and the direct heating at the target site 30 within a predetermined time period. The target site 30 may include at least a cancerous growth and may further include some of the tissue surrounding the cancerous growth. In some embodiments, the apparatus 1 may be configured to provide a non-ionizing alternating magnetic field 15.

As disclosed herein, hyperthermia may be defined as elevation to a temperature above 37.5° C. Accordingly, the apparatuses disclosed herein may be configured to heat a target site to temperatures above 37.5° C. It is noted that hyperthermia is defined as a temperature greater than between 37.5° C. to 38.3° C. (depending on the reference used), occurring without a change in the body's temperature set point. In contrast, hyperpyrexia is an extreme elevation of body temperature which, depending upon the source, is classified as a core body temperature greater than or equal to 40.0 or 41.0° C.; the range of hyperpyrexias include cases considered severe (≥40° C.) and extreme (≥42° C.). It differs from hyperthermia in that one's thermoregulatory system's set point for body temperature is set above normal, then heat is generated by the body to achieve it. In contrast, hyperthermia involves body temperature rising above its set point due to outside factors.

Further, it is noted that thermal ablation is a type of procedure that uses heat, cold, microwave and electrical currents to vaporize (ablate) cancer cells and tumors by heating to above >50° C.

In preferred embodiments, the apparatus is configured to heat the target site to a temperature of between 39° C. and 52° C. (heating to above 39° C. may increase the sensitivity of a cancerous growth to other therapies such as TT-fields, chemotherapy and radiotherapy) and preferably at least 41.1° C. (above which, advantageously, irreversible damage is caused to cells). It is preferred that the heat source is configured to heat the target site to a temperature of at least 42° C. and preferably between 42° C. and 57° C. Heating the target site to a temperature of at least 42° C. induces heating effects on the target site which corresponds to extreme hyperpyrexia.

The heat source 30 may be any suitable heat source for providing direct heating to the target site 30, and may comprise electromagnetic heating, such as capacitive radiofrequency heating, radiative radiofrequency heating, microwave heating, infrared heating and laser heating, heating by ultrasound, heating via a heated fluid, heating by conductive heat emitter, or any other suitable method which heats the target site 30 independently of the non-ionizing alternating electromagnetic field 15. The heat source 30 may be any heat source which heats the target site without the use of a mediator (e.g. directly and not indirectly via a mediator).

In any of the embodiments disclosed herein, the electromagnetic emitter 10 may be configured to provide an electromagnetic field 15 having a frequency of between 10 kHz to 500 kHz and more preferably between 10 kHz and 300 kHz. The electromagnetic field may have a magnetic flux density of between 0.1 pT and 1 mT, or between 0.1 pT and 100 μT, or between 100 μT and 1 mT, and/or the corresponding electric field of between 1 V/cm and 3 V/cm depending on the tissue impedance (i.e. taking into account possible attenuation of the field as it travels from the electromagnetic emitter 10 to the target site 30, which can be determined from the impedance arising from the different types of tissue present between the electromagnetic emitter 10 and the target site 30). As noted above, the electromagnetic field 15 is non-ionizing, and its mechanism on the cancerous site is different to that of ioinizing radiation as discussed in the background section of the present disclosure. Further, the electromagnetic field 15 itself does not provide direct heating to the target site 30 due to the relatively low intensity of the oscillating field.

It will be appreciated that in any of the embodiments disclosed herein the electromagnetic emitter 10 and heat sources may be powered by any power source, and may be powered by the same or different power sources. Likewise, each of the electromagnetic emitter 10 and the heat source 20 may comprise a user interface for selecting the operating parameters of each emitter (frequency, field strength, amplitude, etc), or the emitter 10 and heat source 20 may comprise pre-programmed sequences for emitting electromagnetic radiation and heat according to a predetermined program selectable by the user.

In any of the embodiments disclosed herein, the apparatus may further comprise a thermometry element for measuring the temperature of the target site 30. For example, the apparatus may comprise an implantable thermometry probe configured to be implanted proximal to the target site 30 to measure a temperature indicating the temperature of the target site 30. The probe may comprise, for example, thermocouples, thermistors and/or fibreoptic sensors. In other embodiments, non-invasive thermometry such as infrared sensing, CT thermometry, or magnetic resonance thermometry may be used.

Figure 2:
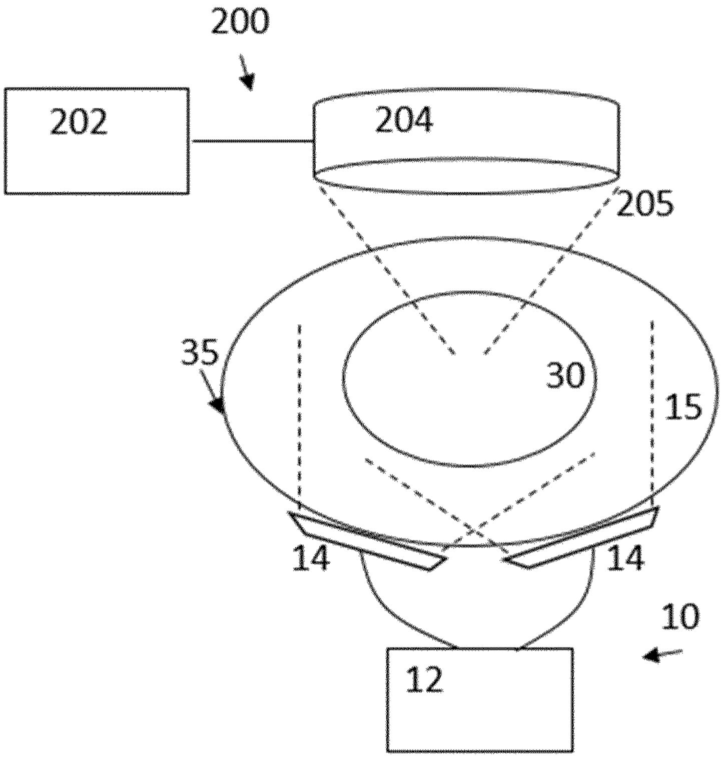
FIG. 2 shows a schematic diagram of an apparatus for treating a cancerous target site according to one or more further embodiments.

FIG. 2 shows a schematic diagram of an electromagnetic emitter 10 and a heat source 200 according to one or more embodiments.

The electromagnetic emitter 10 may comprise one or more sources 12 (such as one or more current or voltage sources) electrically connected to one or more applicators

14. The applicators 14 may be configured to be placed on or proximal to the surface of the patient body 35 and are electrically insulated from the patient body (i.e. do not form a closed electrical circuit between the source 12 and the patient body). In some embodiments, the applicators 14 may comprise one or more electrodes with an electrically insulating coating for preventing electrical contact between the electrodes and the surface of the patient and thus the target site. It is noted that even if the applicators are placed on the surface of the patient of the patient body 35, they remain electrically insulated from the body by, for example, the presence of the electrically insulating coatings. The source 12 may be configured to provide an alternating electromagnetic field to the applicators 14, which in turn produce a magnetic flux density towards the target site 30 to provide the non-ionizing alternating electromagnetic field 15 at the target site 30. It will be appreciated that any number of applicators 14 may be used depending on the type of target site, and the strength of the resulting magnetic flux density at the target site 30 can be readily calculated from the setup by superposition of the electromagnetic fields emitted by each applicator 14. In some embodiments, the applicators 14 may comprise a coil with positive and negative terminals. The one or more sources may be configured to provide an alternating current through the coil to generate a magnetic field out of the coil. The coil may comprise any number of turns, for example 1, 2, 3, 4, 5, 6, 7, 8, 9, 10, 15, 20, 25, 50 or 100, 500 or more.

The heat source 200 shown in FIG. 2 may be an ultrasound emitter and may comprise an ultrasonic source 202 which emits an ultrasonic signal to one or more transducers 204. The transducer 204 is configured to transmit focused ultrasonic radiation 205 to the target site 30. The one or more transducers 204 may include, for example, one or more piezoelectric transducers. The one or more transducers 204 may comprise one or more plastic and/or ceramic transducers. A coupling medium (not shown) may be provided on the patient body 35 between the transducer 204 and the patient body 30 to improve propagation of the ultrasound waves from the transducer 204 to inside the patient body 30 (i.e. to reduce reflections of ultrasound waves). A coupling medium is defined herein as any suitable solid or liquid (or combination thereof) for improving propagation of the ultrasound waves from the transducer 204 to inside the patient body 30. The shape of transducer 204 may be selected in order to select the amount of focusing of the ultrasound, and may be selected to focus the ultrasonic radiation 205 to one or more focal area in the target site 30. For example, the one or more transducers 204 may be 3D printed or otherwise manufacture to a custom shape which is configured to propagate focused ultrasonic radiation to one or more focal areas within the target site 30.

The ultrasound emitter 200 may be configured to provide acoustic energy at frequencies between 0.5 and 10 MHz to provide heating at the target site 30.

In some embodiments, the ultrasound emitter 200 may comprise one or more multi-transducer arrays or phased arrays, planar devices or bowl-shaped sources. Further, the ultrasound emitter 200 may be configured to emit the ultrasound radiation interstitially. That is, the ultrasound emitter 200 may comprise one or more catheter-mounted transducers or other emitting components which are configured to be inserted into the body 35 at or near the target site 30, in order to emit ultrasonic radiation towards one or more points at the target site 30 to provide the required heating.

Whilst FIG. 2 shows a specific configuration of an ultrasound emitter, it is noted that any suitable ultrasonic emitter may be used. For example, any high-intensity focused ultrasound (HIFU) machine may be used, such as MM-guided focused ultrasound.

The ultrasound emitter 200 is configured to emit ultrasound radiation 205 to the target site 30 to cause heating at the target site. In particular, the ultrasound emitter 200 is configured to heating the target site to a predetermined temperature, preferably a temperature of 42° C. or less, and maintain the temperature at the predetermined temperature whilst the electromagnetic field is applied. It will be appreciated that the ultrasound emitter 200 may be configured to heat the target site 30 by providing ultrasound radiation having a predetermined frequency and amplitude which causes the required heating at the target site 30. The ultrasound radiation may be continuous or pulsed wave. For a given frequency, amplitude and type of ultrasonic radiation, the amount of heating at a target site can be determined by routine experimentation.

It will be appreciated for the embodiment of FIG. 2 that the power output of the source 202 as well as the duration of application of the ultrasonic radiation may be selected in order to arrive a predetermined amount of heating at the target site 30. This may be determined by prior empirical measurement or the apparatus may additionally include a thermometer component for measuring the temperature of the target site 30, with heat being applied by the apparatus to achieve and maintain a target temperature at the target site 30.

Figure 3:
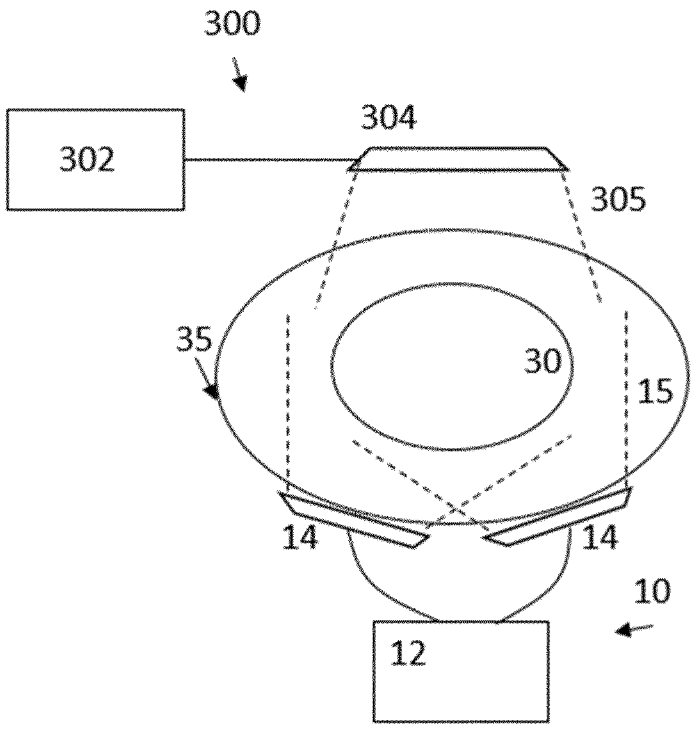
FIG. 3 shows a schematic diagram of an apparatus for treating a cancerous target site according to one or more further embodiments.

FIG. 3 shows a schematic of diagram of an electromagnetic emitter 10 and a heat source 300 according to one or more embodiments. As in the case of FIG. 2, the electromagnetic emitter 10 may comprise one or more electromagnetic sources 12 (such as one or more current or voltage sources) electrically connected to one or more applicators 14. The applicators 14 may be configured to be placed on the surface of the patient body 35. The electromagnetic source 12 may be configured to provide an alternating electromagnetic field to the applicators 14, which in turn produce a magnetic flux density towards the target site 30 to provide the non-ionizing alternating electromagnetic field 15 at the target site 30. It will be appreciated that any number of applicators 14 may be used depending on the type of target site, and the strength of the resulting magnetic flux density at the target site 30 can be readily calculated from the setup by superposition of the electromagnetic fields emitted by each applicator 14.

The heat source 300 comprises one or more antennas or applicators 304 configured to provide an electromagnetic field 305 for providing direct heating to the target site 30. The heat source 300 comprises one or more electromagnetic sources 302 for driving one or more antennas or applicators 304 to provide the heating electromagnetic field 305. The electromagnetic field 305 has a field strength and frequency which causes heating of the target site. The frequency of the electromagnetic field 305 is sufficiently different (e.g. at least an order of magnitude difference) such that the electromagnetic fields 305 and 15 interact with the target site 30 independently (i.e. such that the electromagnetic interference between the fields is negligible). The frequency of the electromagnetic field 305 may be, for example, above 1 MHz to cause dielectric heating of the target site 30 by molecular dipole rotation, polarization and/or vibration, or Ohms law.

The number and configuration of antennas or applicators 304, including their positions, relative amplitudes and phases, can be selected in order to create constructive and/or destructive interference and cause heating only over a particular volume including the target site 30. For example, the antennas or applicators 304 may comprise a single antenna, a pair of antennas, and a 2D or 3D array or phased array of antennas.

In some embodiments, the electromagnetic source 302 is a radiofrequency (RF) source configured to operate at a frequency between 8 and 30 MHz (for example, 8 MHz, 13.56 MHz or 27.12 MHz) to cause capacitive heating. The one or more antennas or applicators 304 comprise a pair of metal applicators with the target site 30 placed between the applicators.

Optionally, the applicators may be coupled to water bolus bags or other media for transferring the field into the body 35. When the RF field is applied to the applicators, power is transferred to the target site 30 and heating is caused. This technique may be used for both superficial and deep tumours by selecting different configurations of applicators to concentrate the resulting electric field at the target site 30. Alternatively, the applicators may be provided as coplanar, or one or more applicators may be configured to be placed inside the body 35 inside insulating catheters. A single applicator may instead be used, coupled to an external ground plane. In all of these configurations, the RF field generated at the target site causes direct heating.

In some embodiments, the electromagnetic source 302 is an RF source configured to operate at frequencies between 60 MHz and 150 MHz. The one or more antennas or applicators 304 comprise one or more antennas placed external to the body. The electromagnetic fields generated at this frequency range penetrate deep into the body and so are suitable for heating of deep target sites 30. Again, the one or more antennas may comprise a pair of antennas with the target site 30 placed between. The antennas may be coupled to water bolus bags or other media for transferring the electromagnetic field into the body 35.

In some embodiments, the electromagnetic source 302 is a microwave (MW) source configured to operate at frequencies between 400 MHz and 2.5 GHz (for example 433 MHz, 915 MHz or 2.45 GHz). The one or more antennas may comprise a pair of antennas or one or more antenna arrays with the target site 30 placed between. The antennas may again be coupled to water bolus bags or other media for transferring the electromagnetic field into the body 35.

It will be appreciated for the embodiment of FIG. 3 that the power output of the source 302 as well as the duration of application may be selected in order to arrive a predetermined amount of heating at the target site 30. This may be determined by prior empirical measurement or the apparatus may additionally include a thermometer component for measuring the temperature of the target site 30, with heat being applied to achieve and maintain a target temperature at the target site 30.

Figure 4:
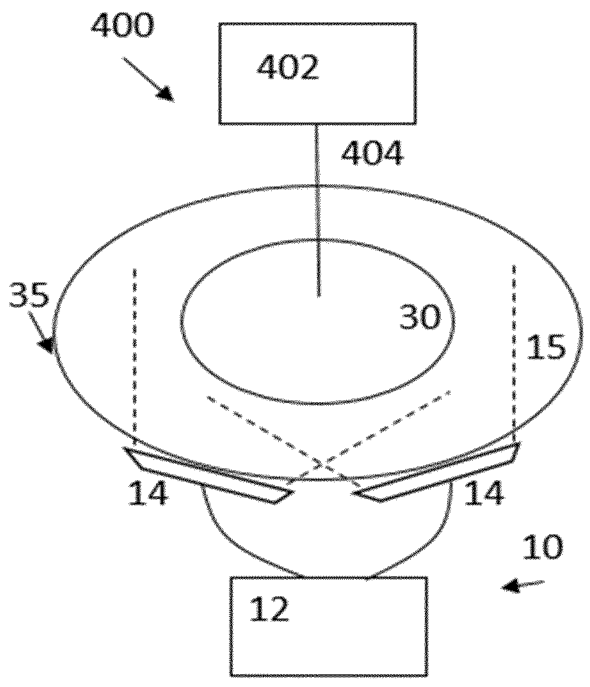
FIG. 4 shows a schematic diagram of an apparatus for treating a cancerous target site according to one or more further embodiments.

FIG. 4 shows a schematic of diagram of an electromagnetic emitter 10 and a heat source 400 according to one or more embodiments. As in the case of FIGS. 2 and 3, the electromagnetic emitter 10 may comprise one or more electromagnetic sources 12 (such as one or more current or voltage sources) electrically connected to one or more applicators 14. The applicators 14 may be configured to be placed on the surface of the patient body 35. The electromagnetic source 12 may be configured to provide an alternating electromagnetic field to the applicators 14, which in turn produce a magnetic flux density towards the target site 30 to provide the non-ionizing alternating electromagnetic field 15 at the target site 30. It will be appreciated that any number of applicators 14 may be used depending on the type of target site, and the strength of the resulting magnetic flux density at the target site 30 can be readily calculated from the setup by superposition of the electromagnetic fields emitted by each applicator 14.

The heat source 400 comprises an electromagnetic source 402 and one or more electromagnetic emitters 404 configured to penetrate the body 35 such that a distal portion of the emitters can be positioned within the target site 30. The one or more emitters 404 are electrically connected to the electromagnetic source 402 so that an electrical current is applied to the one or more emitters 404. The one or more emitters 404 may comprise one or more monopole, dipole, slot or helical coil microwave antennas, resistively-coupled radiofrequency, local current field electrodes or capacitively coupled radiofrequency catheter-based electrodes. Capacitively coupled electrodes may be configured to be contained in low-loss catheters such as a Nylon or Teflon catheter.

In some embodiments, the electromagnetic source 402 is configured to provide an alternating electric current to the one or more emitters 404 in the frequency range of 350 kHz to 30 MHz, which induces an electric current in the area of tissue near the needle(s) and as a result heats the tissue. In other embodiments, the electromagnetic source 402 is configured to provide an alternating electric current to the one or more emitters 404 in the frequency range of 900 MHz to 2.5 GHz (for example 915 MHz or 2.45 GHz), which causes dielectric heating of the tissue surrounding the needle(s).

In other embodiments, the emitters 404 comprise a plurality of electrodes configured to be implanted around the target site 30, and the electromagnetic source 402 is configured to provide a series of very short (e.g. about 100 μs) direct-current electrical pulses between the electrodes. The voltage of the pulses and the positioning of the electrodes are configured to provide a high field strength (e.g. between about 100 V/cm to 3000 V/cm). It has been observed that such pulses provide heating to the target site 30.

It will again be appreciated for the embodiment of FIG. 4 that the power output of the source 402 as well as the duration of application may be selected in order to arrive a predetermined amount of heating at the target site 30. This may be determined by prior empirical measurement or the apparatus may additionally include a thermometer component for measuring the temperature of the target site 30, with heat being applied to achieve and maintain a target temperature at the target site 30.

Figure 5:
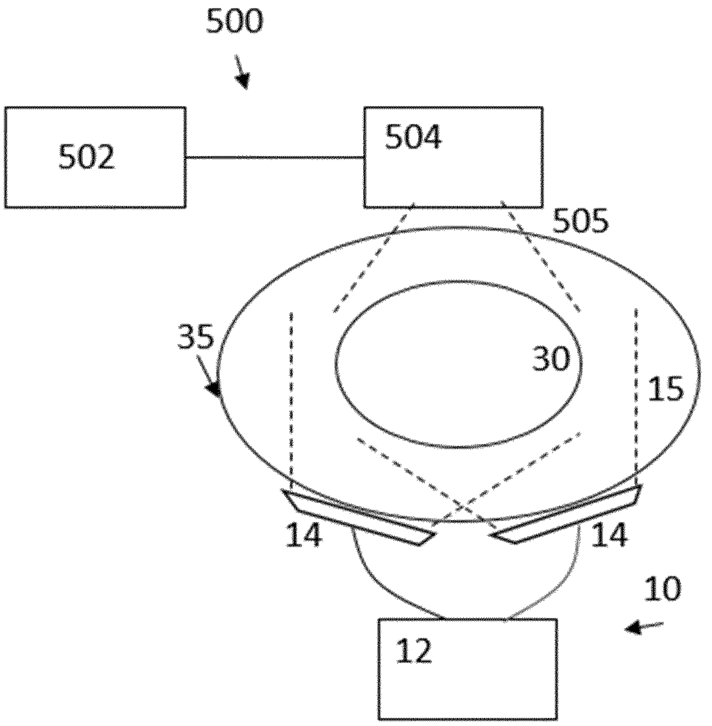
FIG. 5 shows a schematic diagram of an apparatus for treating a cancerous target site according to one or more further embodiments.

FIG. 5 shows a schematic of diagram of an electromagnetic emitter 10 and a heat source 500 according to one or more embodiments. As in the case of FIGS. 2 to 4, the electromagnetic emitter 10 may comprise one or more electromagnetic sources 12 (such as one or more current or voltage sources) electrically connected to one or more applicators 14. The applicators 14 may be configured to be placed on the surface of the patient body 35. The electromagnetic source 12 may be configured to provide an alternating electromagnetic field to the applicators 14, which in turn produce a magnetic flux density towards the target site 30 to provide the non-ionizing alternating electromagnetic field 15 at the target site 30. It will be appreciated that any number of applicators 14 may be used depending on the type of target site, and the strength of the resulting magnetic flux density at the target site 30 can be readily calculated from the setup by superposition of the electromagnetic fields emitted by each applicator 14.

The heat source 500 comprises one or more infrared light source 504 configured to provide infrared radiation 505 to the target site 30, and a power source 502 for powering the one or more infrared lamps. The infrared light source 504 may emit infrared light of any frequency, and in particular frequencies above 300 GHz. The penetration depth of the infrared radiation is typically 1 cm or less, so this apparatus may be suitable for target sites 30 which is located superficially in the body 35.

Again, the power output of the power source 502 as well as the duration of application of the radiation may be selected in order to arrive a predetermined amount of heating at the target site 30. This may be determined by prior empirical measurement or the apparatus may additionally include a thermometer component for measuring the temperature of the target site 30, with heat being applied to achieve and maintain a target temperature at the target site 30.

Figure 6:
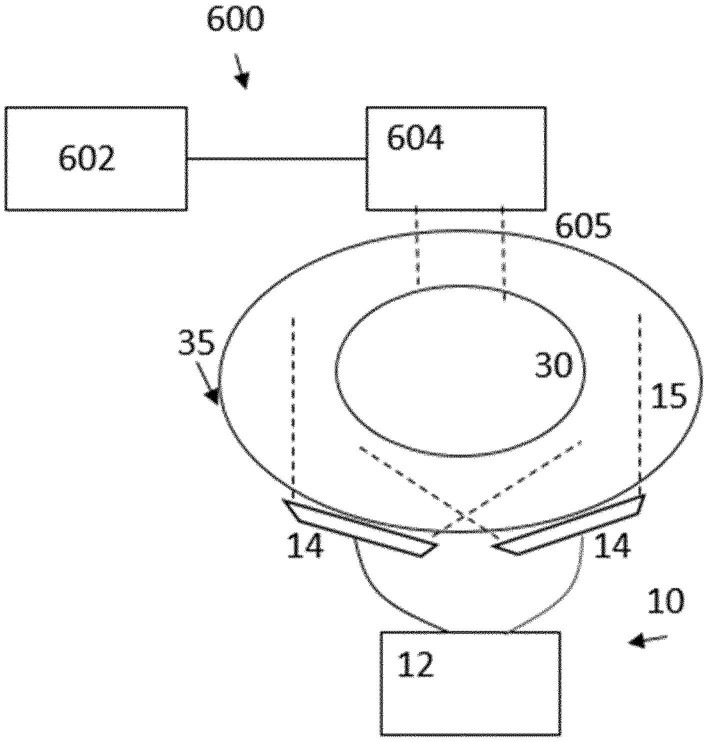
FIG. 6 shows a schematic diagram of an apparatus for treating a cancerous target site according to one or more further embodiments.

FIG. 6 shows a schematic of diagram of an electromagnetic emitter 10 and a heat source 600 according to one or more embodiments. As in the case of FIGS. 2 to 5, the electromagnetic emitter 10 may comprise one or more electromagnetic sources 12 (such as one or more current or voltage sources) electrically connected to one or more applicators 14. The applicators 14 may be configured to be placed on the surface of the patient body 35. The electromagnetic source 12 may be configured to provide an alternating electromagnetic field to the applicators 14, which in turn produce a magnetic flux density towards the target site 30 to provide the non-ionizing alternating electromagnetic field 15 at the target site 30. It will be appreciated that any number of applicators 14 may be used depending on the type of target site, and the strength of the resulting magnetic flux density at the target site 30 can be readily calculated from the setup by superposition the electromagnetic fields emitted by each applicator 14.

The heat source comprises a laser source 604 and a power source 602 configured to power the laser source. The laser source 604 may be configured to emit laser radiation to the target site 30 to cause heating at the target site. The laser radiation may be optically guided, by an optical fiber, directly to the target site to cause local ablation of the target site 30. The laser source 604 may be configured to emit laser radiation having a wavelength of between 900 nm and 1100 nm at any suitable intensity for causing the required heating at the target site 30. The laser source 604 may be configured to operate at between 0.5 W and 15 W power (for example 980 nm at 15 W or 1064 nm at 12 W). The laser source 604 may be moved rotationally and linearly to target multiple regions in one or more target sites 30.

The power output of the power source 602 as well as the duration of application of the laser radiation may be selected in order to arrive a predetermined amount of heating at the target site 30. This may be determined by prior empirical measurement or the apparatus may additionally include a thermometer component for measuring the temperature of the target site 30, with heat being applied to achieve and maintain a target temperature at the target site 30. For example, the apparatus may include an Mill machine to perform magnetic resonance thermometry to monitor the temperature of the target site 30 during the heating process.

Figure 7:
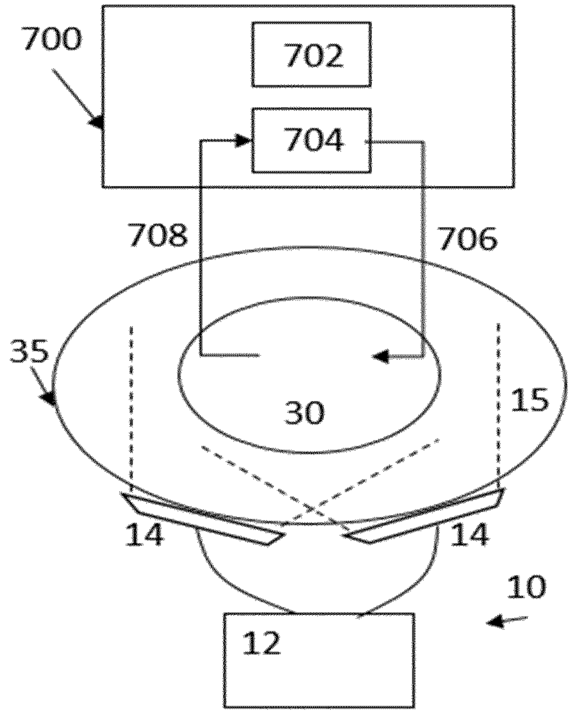
FIG. 7 shows a schematic diagram of an apparatus for treating a cancerous target site according to one or more further embodiments.

FIG. 7 shows a schematic of diagram of an electromagnetic emitter 10 and a heat source 700 for heating the target site 30 according to one or more embodiments. As in the case of FIGS. 2 to 6, the electromagnetic emitter 10 may comprise one or more electromagnetic sources 12 (such as one or more current or voltage sources) electrically connected to one or more applicators 14. The applicators 14 may be configured to be placed on the surface of the patient body 35. The electromagnetic source 12 may be configured to provide an alternating electromagnetic field to the applicators 14, which in turn produce a magnetic flux density towards the target site 30 to form the non-ionizing alternating electromagnetic field 15 at the target site 30. It will be appreciated that any number of applicators 14 may be used depending on the type of target site, and the strength of the resulting magnetic flux density at the target site 30 can be readily calculated from the setup by superposition of the electromagnetic fields emitted by each applicator 14.

The heat source 700 comprises a heater 702, a pump 704, a fluidic output 706 and a fluidic input 708. The fluidic output 706 is configured to fluidically connect to a part the body 35 which is upstream from the target site 30, and the fluidic input 708 is configured to fluidically connect to a part of the body 35 which is downstream from the target site 30. When connected, a fluidic loop is created from the target site 30 to the pump 704 and back to the target site 30 again. The fluidic loop may be configured to be created in any fluidic system of the body 35 (e.g. vascular, renal or similar). The heater 702 is configured to heat the fluid to a desired temperature as it passes through the heat source 700, which is then delivered to the target site 30 via fluidic output 706. Accordingly, the fluidic loop provides a continuous source of heated fluid to the target site 30. It is noted that the fluid may be the patient's blood or additionally the heat source 700 may comprise a reservoir of fluid (not shown) which is configured to be heated and added to the fluidic loop. For example, the fluid may comprise a chemotherapeutic composition, anti-cancer drug or similar or may comprise a biocompatible solution such as saline solution or similar.

The heater 702 may be any suitable heater, such as a resistive heater, or an electromagnetic heater configured to heat the fluid by the emission of, for example, microwave radiation. The heater 702 may be situated externally to the body 35 or may be configured to be implanted in the body 35.

The amount of heat provided by the heat source 700 as well as the duration of application of the heat source 700 may be selected in order to arrive a predetermined amount of heating at the target site 30. This may be determined by prior empirical measurement or the apparatus may additionally include a thermometer component for measuring the temperature of the target site 30, with heat being applied to achieve and maintain a target temperature at the target site 30.

Figure 8:
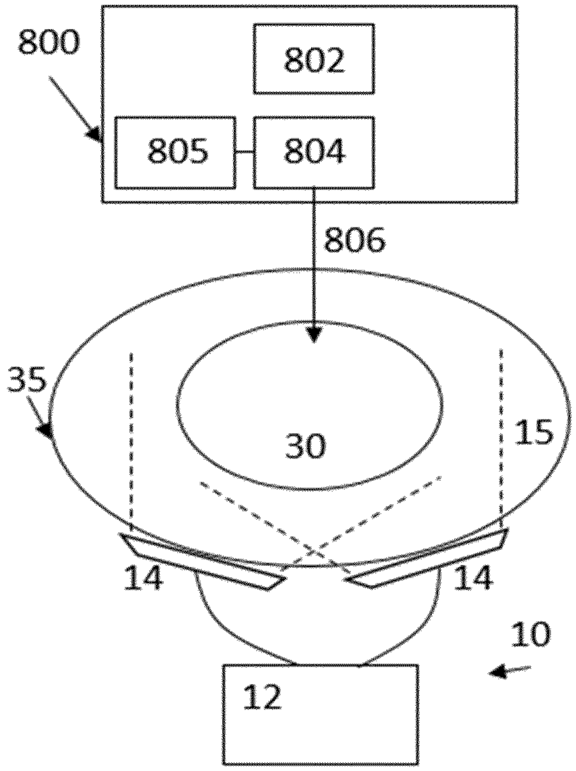
FIG. 8 shows a schematic diagram of an apparatus for treating a cancerous target site according to one or more further embodiments.

FIG. 8 shows a schematic of diagram of an electromagnetic emitter 10 and a heat source 800 for heating the target site 30 according to one or more embodiments. As in the case of FIGS. 2 to 7, the electromagnetic emitter 10 may comprise one or more electromagnetic sources 12 (such as one or more current or voltage sources) electrically connected to one or more applicators 14. The applicators 14 may be configured to be placed on the surface of the patient body 35. The electromagnetic source 12 may be configured to provide an alternating electromagnetic field to the applicators 14, which in turn produce a magnetic flux density towards the target site 30 to provide the non-ionizing alternating electromagnetic field 15 at the target site 30. It will be appreciated that any number of applicators 14 may be used depending on the type of target site, and the strength of the resulting magnetic flux density at the target site 30 can be readily calculated from the setup by superposition of the electromagnetic fields emitted by each applicator 14.

The heat source 800 comprises a heater 802, a reservoir 805, a pump 804 and a fluidic output 806. The fluidic output 806 is configured to be fluidically connected to the target site 30. In use, the pump 804 is configured to pump fluid in the reservoir 805 to the target site 30 via fluidic output 806. The heater 802 is configured to heat the fluid in the reservoir 805 to a desired temperature before the fluid is pumped to the target site 30. The fluid may comprise a chemotherapeutic composition, anti-cancer drug or similar or may comprise a biocompatible solution such as saline solution or similar.

The amount of heat provided by the heat source 800, the amount of fluid provided from the reservoir 805 and the duration of application of the heat source 800 may be selected in order to arrive a predetermined amount of heating at the target site 30. This may be determined by prior empirical measurement or the apparatus may additionally include a thermometer component for measuring the temperature of the target site 30, with heat being applied to achieve and maintain a target temperature at the target site 30.

Figure 9:
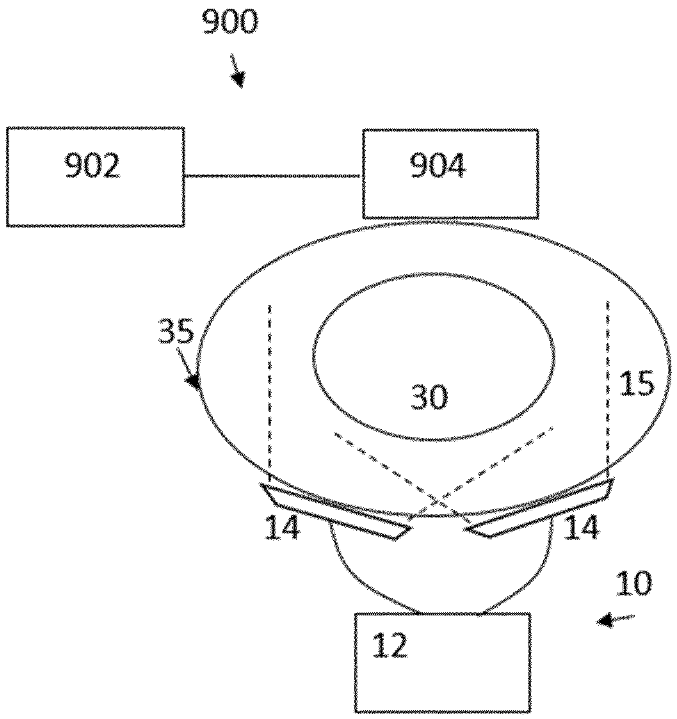
FIG. 9 shows a schematic diagram of an apparatus for treating a cancerous target site according to one or more further embodiments.

FIG. 9 shows a schematic of diagram of an electromagnetic emitter 10 and a heat source 900 for heating the target site 30 according to one or more embodiments. As in the case of FIGS. 2 to 8, the electromagnetic emitter 10 may comprise one or more electromagnetic sources 12 (such as one or more current or voltage sources) electrically connected to one or more applicators 14.

The applicators 14 may be configured to be placed on the surface of the patient body 35. The electromagnetic source 12 may be configured to provide an alternating electromagnetic field to the applicators 14, which in turn produce a magnetic flux density towards the target site 30 to provide the non-ionizing alternating electromagnetic field 15 at the target site 30. It will be appreciated that any number of applicators 14 may be used depending on the type of target site, and the strength of the resulting magnetic flux density at the target site 30 can be readily calculated from the setup by superposition of the electromagnetic fields emitted by each applicator 14.

Heat source 900 comprises a heat emitter 904 configured to provide conductive heating to the target site 30. The heat source may comprise a power source 902 to power the heat emitter 904 (such as an electrical power source), or the heat emitter 904 may be pre-heated or chemically self-heating (e.g. by exothermic chemical reaction). The heat emitter 904 may be provided on the surface of the body 35, or may be configured to be implanted inside the body to provide heat to the target site 30 at a location proximal to the target site. For example, the heat emitter 904 may be an implantable resistive heater configured to be powered by an electrical power source 902. The heat emitter 904 may be configured to heat a local region of the body 35 or it may be configured to heat the entire body 35.

The amount of heat provided by the heat source 900, and the duration of application of the heat source 900 may be selected in order to arrive a predetermined amount of heating at the target site 30. This may be determined by prior empirical measurement or the apparatus may additionally include a thermometer component for measuring the temperature of the target site 30, with heat being applied to achieve and maintain a target temperature at the target site 30.

Figure 10:
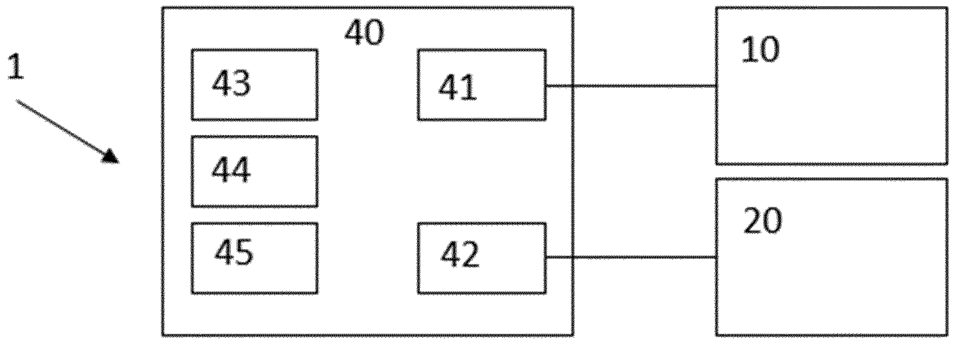
FIG. 10 shows a schematic of an apparatus for treating a cancerous target site according to one or more embodiments.

FIG. 10 shows a schematic of an apparatus 1 for treating a cancerous target site according to one or more embodiments. As in the case of FIG. 1, the apparatus comprises an electromagnetic emitter 10 and a heat source 20. The electromagnetic emitter 10 is configured to provide a magnetic flux density at the target site. The heat source 20 is configured to provide direct heating at the target site to cause hyperthermia at the target site by any of the above mechanisms disclosed herein. In one configuration, the apparatus 1 is configured to provide the non-ionizing alternating electromagnetic field and the direct heating at the target site simultaneously. The electromagnetic emitter 10 and the heat source 20 may take any suitable configuration and may take the configurations shown in FIGS. 2 to 9.

The apparatus 1 shown in FIG. 10 further comprises a controller 40 for controlling the emitter 10 and heat source 20. The controller comprises a first control interface 41 for controlling the operation of the electromagnetic emitter 10 and a second control interface 42 for controlling the operation of the heat source 20. The controller 40 is configured to provide control signals to the emitter 10 and heat source 20 via the control interfaces 41 and 42. The emitter 10 and heat source 20 may receive the control signals by any suitable form of communication, either wired or wireless, such as optic, fiber-optic, ethernet or similar, or any suitable wireless communication. The controller 40 may further be configured to power one or more of the emitter 10 and heat source 20, or one or more of the emitter 10 and heat source 20 may be powered independently of controller 40.

The controller 40 further comprises one or more of a user interface 43, memory 44 and processor 45. The user interface 43 allows a user to control operation of the emitter 10 and heat source 20 manually, for example by controlling the operating parameters of the emitter 10 and heat source 20, and switching on or off their operation. The user interface 43 may allow the user to select a sequence of operation of the emitter 10 and heat source 20 over a time period. The memory 44 may contain instructions, which when executed using the processor 45, cause the emitter 10 and heat source 20 to be operated according to any suitable sequence including the sequences of operation disclosed herein.

The memory 44 may comprise one or more volatile or non-volatile memory devices, such as DRAM, SRAM, flash memory, read-only memory, ferroelectric RAM, hard disk drives, floppy disks, magnetic tape, optical discs, or similar. Likewise, the processor 45 may comprise one or more processing units, such as a microprocessor, GPU, CPU, multi-core processor or similar.

The controller 40 may further be implemented in software, hardware, or any combination in order to execute the sequences of operation disclosed herein.

Figure 11:
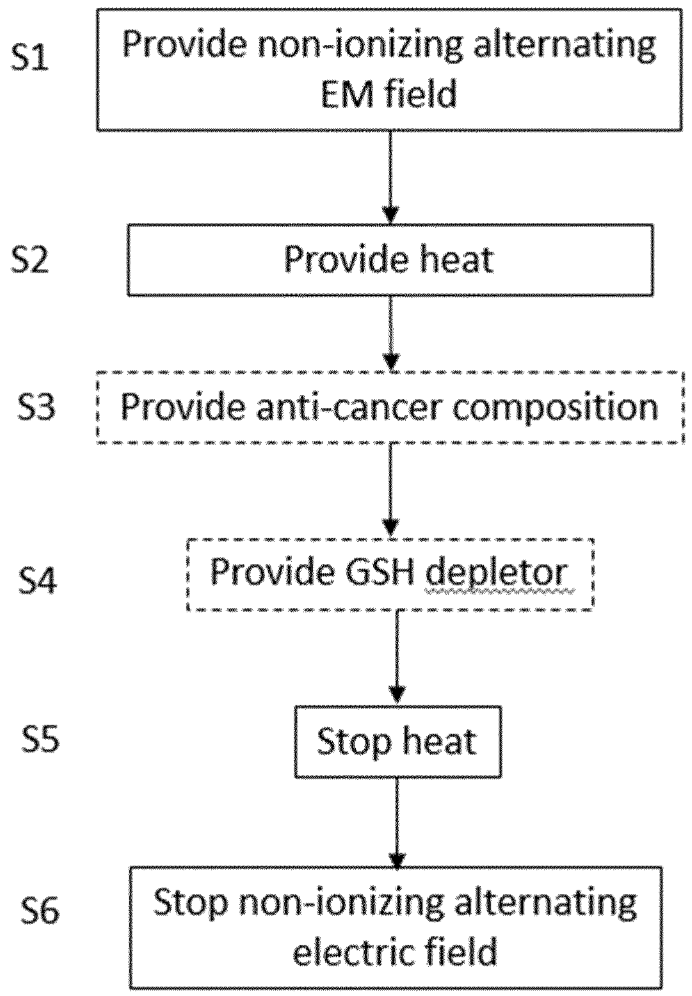
FIG. 11 shows a schematic of a method for treating a cancerous target site using an apparatus according to the disclosure.

FIG. 11 shows a schematic of a method for treating a cancerous target site using an apparatus according to the disclosure. The apparatus may take any configuration disclosed herein. Before the method of FIG. 11 is implemented, the emitter 10 and heat source 20 may be suitably positioned on the patient. For example, the applicators of the electromagnetic emitter 10 may be placed at predetermined points on the patient's body and the heat source 20 (for example the transducer 24) may also be suitably positioned.

In step S1, the non-ionizing alternating electromagnetic field is provided to give a magnetic flux density at the target site using electromagnetic emitter 10.

In step S2, the heat (and more particularly direct heat) is provided to the target site using heat source 20. This may be provided whilst the electromagnetic field is also being provided to the target site 30 or within a predetermined time before or after the electromagnetic field is provided. In some embodiments, it may be that only the alternating electromagnetic field is provided to produce the magnetic flux density at the target site without the heating for a first time period, before both are provided simultaneously to the target site.

Optionally, in step S3, an anti-carcinogenic composition is provided to the target site. The anti-carcinogenic composition may be administered by any suitable means, such as orally or intravenously. It is noted that the anti-carcinogenic composition may be provided before or simultaneously to steps S1, S2 and step S4 or a predetermined time after step S1, S2 or S4.

The term "anti-carcinogenic composition", as used herein, refers to a composition that comprises an agent that at least partially inhibits the development or progression of a cancer, including inhibiting in whole or in part symptoms associated with the cancer. The term "cancer", a used herein, refers to a disease characterized by uncontrolled cell division (or by an increase of survival or apoptosis resistance) and by the ability of said cells to invade other neighbouring tissues (invasion) and spread to other areas of the body where the cells are not normally located (metastasis) through the lymphatic and blood vessels, circulate through the bloodstream, and then invade normal tissues elsewhere in the body. Depending on whether or not they can spread by invasion and metastasis, tumours are classified as being either benign or malignant: benign tumours are tumours that cannot spread by invasion or metastasis, i.e., they only grow locally; whereas malignant tumours are tumours that are capable of spreading by invasion and metastasis. The anti-carcinogenic composition may comprise one or more anti-carcinogenic compositions, including one or more of those disclosed in relation to FIGS. 12 to 27.

As used herein, the term cancer, is preferably directed to solid tumours and/or infiltrating tumours.

As used herein, a "solid tumour" is understood as an abnormal mass of tissue that usually does not contain cysts or liquid areas. Different types of solid tumours are named for the type of cells that form them. Examples of solid tumours are sarcomas, carcinomas, and lymphomas. Leukemias (cancers of the blood) generally do not form solid tumours.

As used herein, an "infiltrating tumour" is understood as tumours that have abnormal structures of tumours that show, at the same time, clear growing nodules and infiltrating growth.

Preferably the invention is directed to cancers including, but not limited to, the following types: breast cancer; biliary tract cancer; bladder cancer; brain cancer including glioblastomas, in particular glioblastoma multiforme, and medulloblastomas; cervical cancer; head and neck carcinoma; choriocarcinoma; colon cancer, colorectal cancer; endometrial cancer; esophageal cancer; gastric cancer; intraepithelial neoplasms including Bowen's disease and Paget's disease; liver cancer, hepatoma; lung cancer, pleural mesothelioma; oral cancer including squamous cell carcinoma; parotid gland cancer; ovarian cancer including those arising from epithelial cells, stromal cells, germ cells and mesenchymal cells; pancreatic cancer; prostate cancer; kidney cancer, suprarenal cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; cervix cancer, endometrial cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor.

In a particular embodiment, the cancer is melanoma. The term "melanoma", as used herein, refers to a malignant skin tumour of melanocytes and includes, but is not limited to, melanomas, metastatic melanomas, melanomas derived from either melanocytes or melanocyte related nevus cells, melanocarcinomas, melanoepitheliomas, melanosarcomas, melanoma in situ, superficial spreading melanoma, modular melanoma, lentigo malignant melanoma, acral lentiginous melanoma, invasive melanoma and familial atypical mole and melanoma (FAM-M) syndrome. Moreover, the term "melanoma" refers not only to primary melanomas but also to "melanoma metastasis" which, as used herein, refers to the spread of melanoma cells to regional lymph nodes and/or distant organs. This event is frequent, given that melanomas contain multiple cell populations characterized by diverse growth rates, karyotypes, cell-surface properties, antigenicity, immunogenicity, invasion, metastasis, and sensitivity to cytotoxic drugs or biologic agents. Melanoma shows frequent metastasis to brain, lungs, lymph nodes, and skin. Other cancers will-be known to one of ordinary skill in the art.

Figure 12:
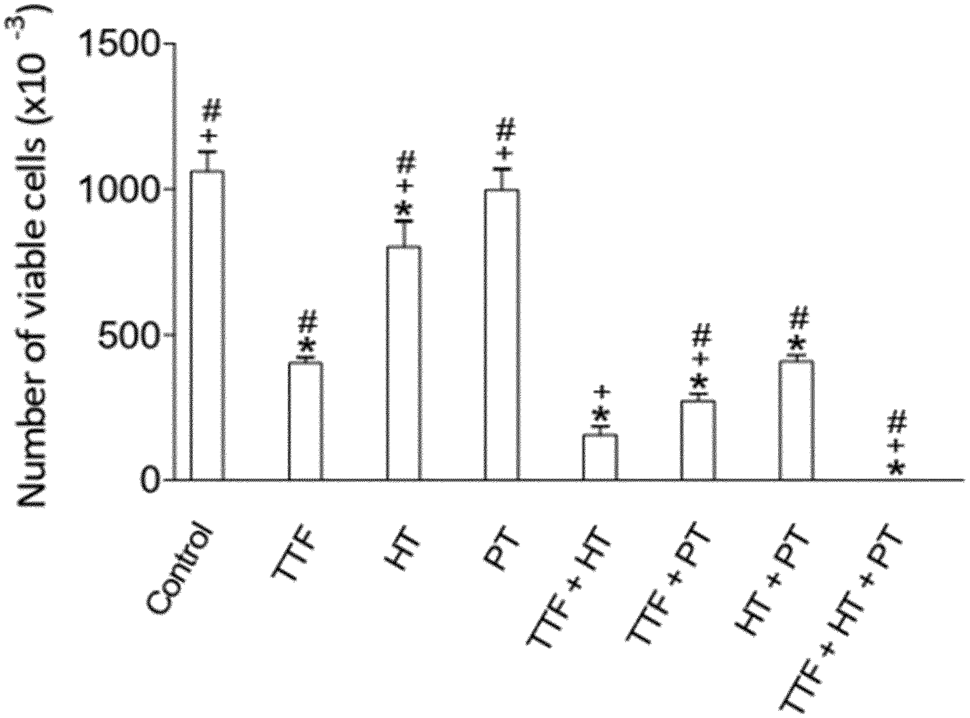
FIG. 12 shows experimental data showing the in vitro effect of TT-Fields ("TTF"), hyperthermia ("HT"), pterostilbene ("PT") and their combinations on U87MG cells. The TT-Field applied was at 300 kHz for 240 mins (from minute 0 to minute 240) for an average magnetic flux density of 8 μT. The hyperthermia applied was 42° C. for 10 minutes (from minute 120 to minute 130). 20 uM of pterostilbene was applied for 120 minutes (from minute 120 to minute 240). The data shows mean number of viable cells for 5 experiments, with $P<0.01$ using Student's t test vs the control for those labelled *, vs TTF for those labelled + and vs TTF+HT for those labelled #.

FIG. 12 shows experimental data showing the in vitro effect of TT-Fields ("TTF"), hyperthermia ("HT"), pterostilbene ("PT") and their combinations on U87MG cells. The TT-Field applied was at 300 kHz for 240 mins (from minute 0 to minute 240) for an average magnetic flux density of 8 μT. The hyperthermia applied was 42° C. for 10 minutes (from minute 120 to minute 130). 20 μM of pterostilbene was applied for 120 minutes (from minute 120 to minute 240). The data shows mean number of viable cells for 5 experiments, with $P<0.01$ using Student's t test vs the control for those labelled *, vs TTF for those labelled + and vs TTF+HT for those labelled #. The magnetic field was applied using a solenoid with approximately 100 μT magnetic flux density at the central axis of the solenoid. The solenoid was placed at a distance from the cell cultures such that the average field strength on the surface of the culture flasks where the cells were attached was 8 μT.

It is noted that, as already indicated previously, and as it can be seen in FIG. 12, it has been found hyperthermia potentiates the anti-cancer effect of the non-ionizing alternating electromagnetic field (TT-Field). In particular, the combination permits a much lower temperature (42° C. or less) for the hyperthermia whilst still reducing cell viability. This also means that a larger volume of tissue heated by the hyperthermia can be targeted. Accordingly, the apparatuses disclosed herein provides an effective method of treating cancerous sites by applying a TT-Field and direct heating of the cancerous site (i.e. not via a mediator). Further, as shown in FIG. 12 the combination of a TT-Field, hyperthermia and pterostilbene effectively eliminates all cells in vitro. The combined therapy is not expected to have any substantial side effects in vivo as the amount of pterostilbene use is well-tolerated in vivo.

Figure 13:
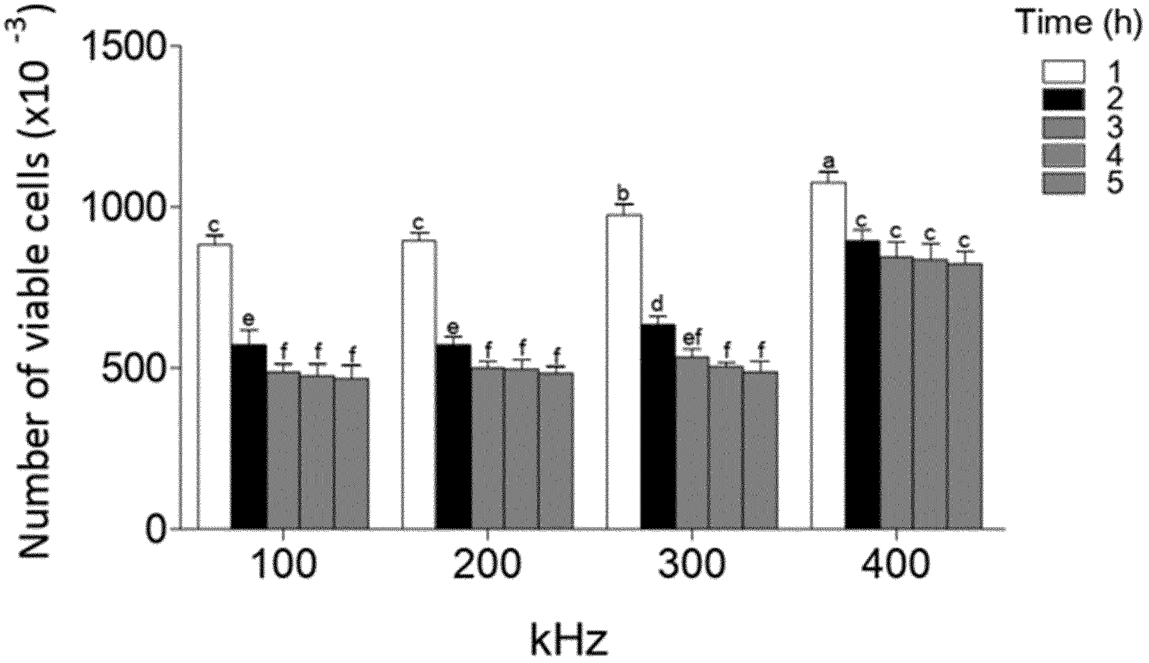
FIG. 13 shows in vitro experimental data for the for the effect on cell viability for U87MG (ATCC) cells when exposed to an oscillating magnetic field.

FIG. 13 shows in vitro experimental data for the effect on cell viability for U87MG (ATCC) cells when exposed to various oscillating magnetic fields. Different cell cultures were exposed to one of the following magnetic fields: 24 μT at a frequency of 100 kHz; 12 μT at a frequency of 200 kHz; 8 μT at a frequency of 300 kHz; or 6 μT at a frequency of 400 kHz. Cell viability for each frequency after 1, 2, 3, 4 and 5 hours was measured. Five independent experiments were performed for each frequency and time point. The data for each frequency shows the average cell viability and standard deviation over time (1 to 5 hours from left to right) for the 5 corresponding experiments. A two-ways analysis of variance (ANOVA) was used to make comparisons among the different groups. It can be seen that cell viability is reduced for all frequencies, and the effect is further increased for frequencies equal to or below 300 kHz. Letters "a" to "f" are assigned to the data based on statistical tests applied to the data. Data labelled with the same letter are considered statistically similar, whereas data assigned different letters are considered significantly different with P less than 0.01.

FIG. 14 shows in vitro experimental data for the effect on cell viability for U87MG cells when exposed to heat. Different cell cultures were heated to temperatures of 37, 38, 39, 40, 41 or 42° C. Five independent experiments were performed for each temperature and time point. The data for each temperature shows the average cell viability and standard deviation of the five corresponding experiments after 5 and 10 minutes of exposure to the temperature. Hyperthermia equivalent to a very high fever (41° C. or above) reduced the viability of U87MG cells significantly. The data labelled * indicates a P value (student's t test) less than 0.01 compared to the 37° C. data at the corresponding time, and the data labelled + indicates a P value less than 0.01 for the data at 10 minutes compared to the data at 5 mins for the same temperature.

FIGS. 15B to 15F show microscopic images of in vitro U87MG cell cultures after exposed to different external treatments. FIG. 15A shows a microscopic image of a control vitro U87MG cell culture which was not exposed to any external treatments and maintained at the physiological internal temperature of 37° C. FIG. 15B shows a cell culture after being exposed to an electromagnetic field having a magnetic flux density of about 8 μT at 300 kHz from 0 to 240 minutes. FIG. 15C shows a cell culture after being exposed to heating to 42° C. for 10 minutes from minute 120 to 130. FIG. 15D shows a cell culture after being exposed to 20 μM pterostilbene from minute 120 to minute 240. FIG. 15E shows a cell culture after exposure to an electromagnetic field having a magnetic flux density of about 8 μT at 300 kHz from 0 to 240 minutes and 20 μM pterostilbene from minute 120 to minute 240. FIG. 15F shows a cell culture after exposure to an electromagnetic field having a magnetic flux density of about 8 μT at 300 kHz from 0 to 240 minutes, heating to 42° C. for 10 minutes from minute 120 to 130 and 20 μM pterostilbene (PT) from minute 120 to minute 240. It is noted that the combination of TTF+HT+PT completely eliminates all U87MG growing cells. This therapy shows the same effectiveness in other glioblastoma lines such as C6 and GL261.

Figure 16:
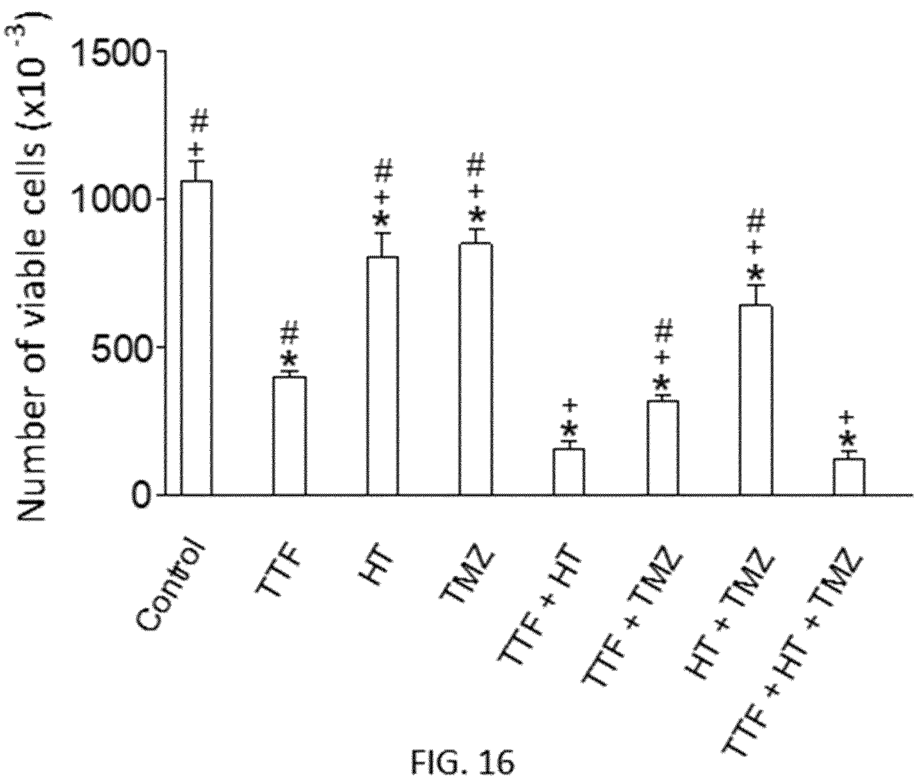
FIG. 16 shows in vitro experimental data for the effect on cell viability for U87MG cells when exposed to an electromagnetic field, heat and temozolomide (TMZ)

FIG. 16 shows in vitro experimental data for the effect on cell viability for U87MG cells when exposed to an electromagnetic field having a magnetic flux density of about 8 μT at 300 kHz for about 240 minutes (data labelled "TTF"), a temperature of 42° C. for about 10 minutes (data labelled HT), 50 μM Temozolomide (data labelled "TMZ"), and combinations thereof. The data show mean values for five independent experiments. Data labelled * indicates a P value (student's t test) less than 0.01 compared to control. Data labelled + indicates a P value (student's t test) less than 0.01 compared to the TTF-only data. Data labelled # indicates a P value (student's t test) less than 0.01 compared to the TTF+HT data.

Figure 17:
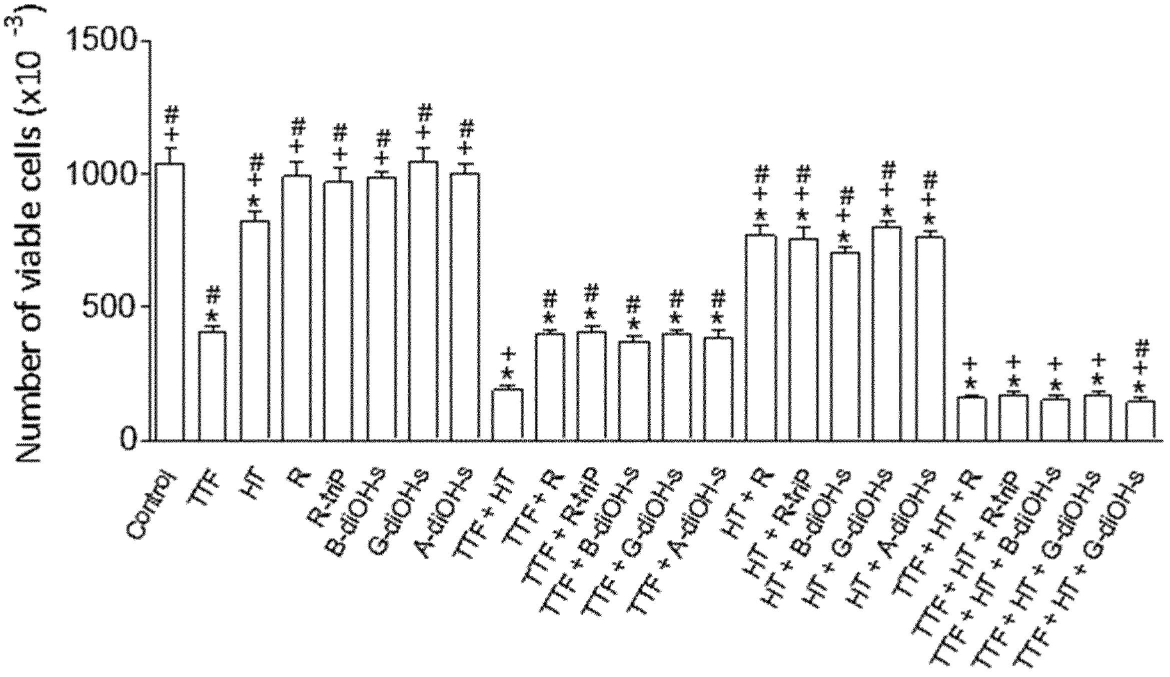
FIG. 17 shows in vitro experimental data for the effect on cell viability for U87MG cells when exposed to an electromagnetic field, heat and resveratrol or its derivatives.

FIG. 17 shows in vitro experimental data for the effect on cell viability for U87MG cells when exposed to an electromagnetic field having a magnetic flux density of about 8 μT at 300 kHz for about 240 minutes (data labelled "TTF"), a temperature of 42° C. for about 10 minutes (data labelled HT) at minute 120 to 130, 20 μM resveratrol at minute 210 to 240 (data labelled "R"), 20 μM resveratrol triphosphate at minute 210 to 240, (data labelled "R-triP"), 20 μM 4'-butyrate-3,5-dihydroxystilbene at minute 210 to 240, (data labelled "B-diOH-s"), 20 μM 3-glucoside-5,4'-dihydroxystilbene at minute 210 to 240, (data labelled "G-diOH-s"), 20 μM 3-amide-5,4'-dihydroxystilbene at minute 210 to 240, (data labelled "A-diOH-s"), and combinations thereof. The data are means with standard deviation for four independent experiments. Data labelled * indicates a P value (student's t test) less than 0.01 compared to the control. Data labelled + indicates a P value (student's t test) less than 0.01 compared to the TTF-only data. Data labelled # indicates a P value (student's t test) less than 0.01 compared to the TTF+HT data. It is observed that resveratrol and its derivatives do not eliminate all U87MG cell growing in vitro, although it is observed that a significant reduction in cell viability occurs for TTF+HT+G-diOH-s.

The effectiveness of therapy by heating in combination with tumour treating fields and exposure to PT is also observed in other cell lines in vitro, such as A2058 (melanoma), AsPC-1 (pancreas carcinoma), A549 (lung carcinoma), MCF-7 (mammary gland carcinoma), HT-29 (colorectal carcinoma), PC-3 (prostate carcinoma), SK-OV-3 (ovarian carcinoma and HepG2 (hepatocarcinoma).

Figure 18:
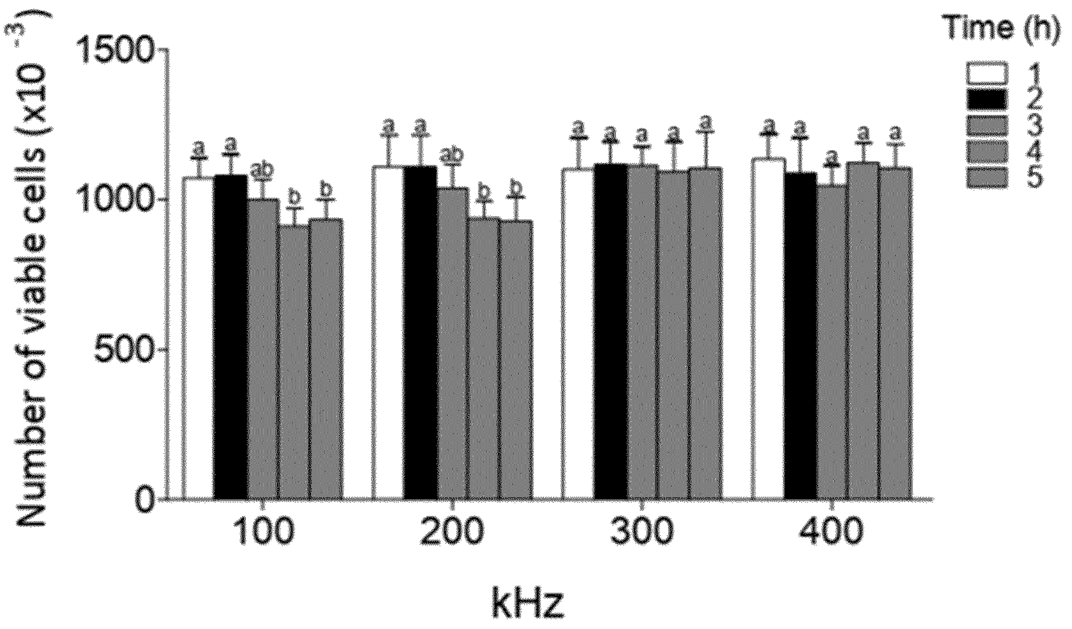
FIG. 18 shows the shows in vitro experimental data for the effect on cell viability for AsPC1 (pancreatic adenocarcinoma, ATCC) cells when exposed to an oscillating magnetic field.

FIG. 18 shows the shows in vitro experimental data for the effect on cell viability for AsPC1 (pancreatic adenocarcinoma, ATCC) cells when exposed to various oscillating magnetic fields. Different cell cultures were exposed to one of the following magnetic fields: 2 μT at 100 kHz; 1.5 μT at 200 kHz; 0.7 μT at 300 kHz; or 0.5 μT at 400 kHz, Cell viability for each frequency after 1, 2, 3, 4 and 5 hours was measured for each cell culture. Five independent experiments were performed for each frequency and time point. The data for each frequency shows the average cell viability and standard deviation over time (1 to 5 hours from left to right) for the 5 corresponding experiments. A two-ways analysis of variance (ANOVA) was used to make comparisons among the different groups. It can be seen that cell viability is reduced for frequencies equal to or below 200 kHz. Letters "a" and "b" are assigned to the data based on statistical tests applied to the data. Data labelled with the same letter are considered statistically similar, whereas data assigned different letters are considered significantly different with P less than 0.01.

Figure 19:
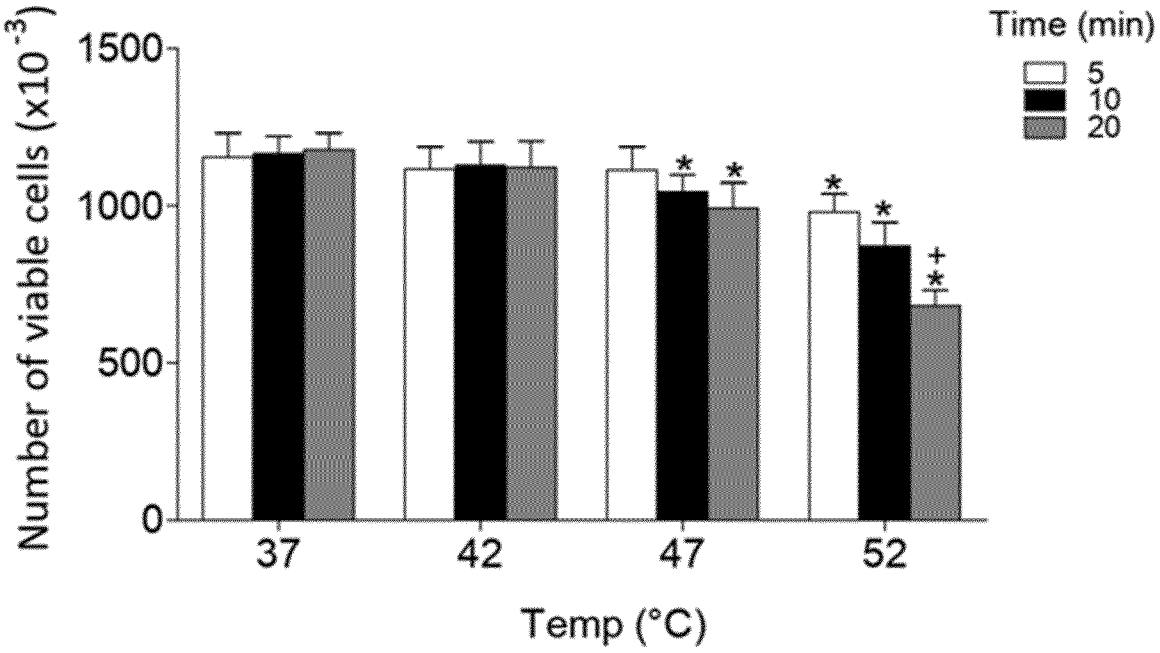
FIG. 19 shows in vitro experimental data for the effect on cell viability for AsPC1 cells when exposed to heat.

FIG. 19 shows in vitro experimental data for the effect on cell viability for AsPC1 cells when exposed to heat. Different cell cultures were heated to temperatures of 37, 42, 47 or 52° C. Five independent experiments were performed for each temperature and time point. The data for each temperature shows the average cell viability and standard deviation of the five corresponding experiments after 5, 10 and 20 minutes of exposure to the temperature. Heating to 47° C. or above reduced the viability of AsPC1 cells significantly. The data labelled * indicates a P value (student's t test) less than 0.01 compared to the 37° C. data at the corresponding time, and the data labelled + indicates a P value less than 0.01 for the data at 10 and 20 minutes compared to the data at 5 mins for the same temperature.

Figure 20:
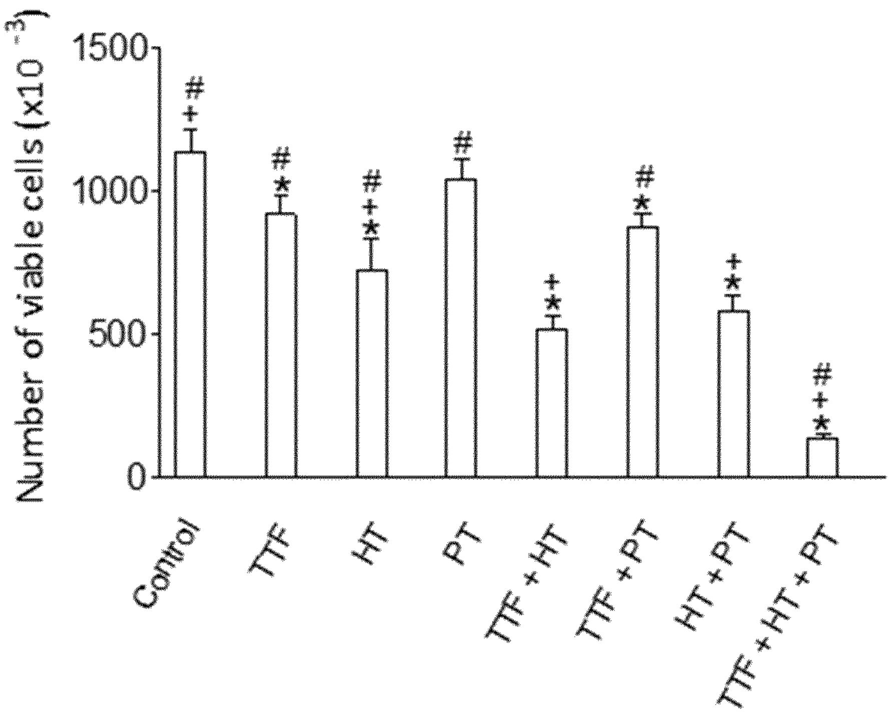
FIG. 20 shows experimental data showing the in vitro effect of TT-Fields ("TTF"), hyperthermia ("HT"), pterostilbene ("PT") and their combinations on AsPC1 cells.

FIG. 20 shows experimental data showing the in vitro effect of TT-Fields ("TTF"), hyperthermia ("HT"), pterostilbene ("PT") and their combinations on AsPC1 cells. For TTF data the TT-Field applied was at 200 kHz for 240 mins (from minute 0 to minute 240) for a field intensity of 1.5 μT. For HT data the hyperthermia applied was 52° C. for 20 minutes (from minute 120 to minute 140). For PT data 20 uM of pterostilbene was applied from minute 0 to minute 240. The data shows mean number of viable cells for 5 experiments, with $P<0.01$ using Student's t test vs the control for those labelled *, vs TTF for those labelled + and vs TTF+HT for those labelled #.

FIGS. 21B to 21H show microscopic images of in vitro AsPC1 cell cultures after exposed to different external treatments. FIG. 21A shows a microscopic image of a control vitro AsPC1 cell culture which was not exposed to any external treatments and maintained at an optimum temperature for AsPC1. FIG. 21B shows a cell culture after being exposed to an electromagnetic field having a magnetic flux density of about 1.5 μT at 200 kHz from 0 to 240 minutes. FIG. 21C shows a cell culture after being exposed to heating to 52° C. for 20 minutes from minute 120 to 140. FIG. 21D shows a cell culture after being exposed to 20 μM pterostilbene from minute 0 to minute 240. FIG. 21E shows a cell culture after exposure to an electromagnetic field having a magnetic flux density of about 1.5 μT at 200 kHz from 0 to 240 minutes and heating to 52° C. for 20 minutes from minute 120 to 140. FIG. 21F shows a cell culture after exposure to an electromagnetic field having a magnetic flux density of about 1.5 μT at 200 kHz from 0 to 240 minutes and 20 μM pterostilbene (PT) from minute 0 to minute 240. FIG. 21G shows a cell culture after exposure to an electromagnetic field having a magnetic flux density of about 1.5 μT at 200 kHz from 0 to 240 minutes, heating to 52° C. for 20 minutes from minute 120 to 140 and 20 μM pterostilbene (PT) from minute 0 to minute 240. FIG. 21H shows the cell culture of FIG. 21G after 24 hours where cultured cells were maintained at 37° C. without any treatment. The growing cells do not seem to recover 24 hours after the combined treatment of FIG. 21G.

Figure 22:
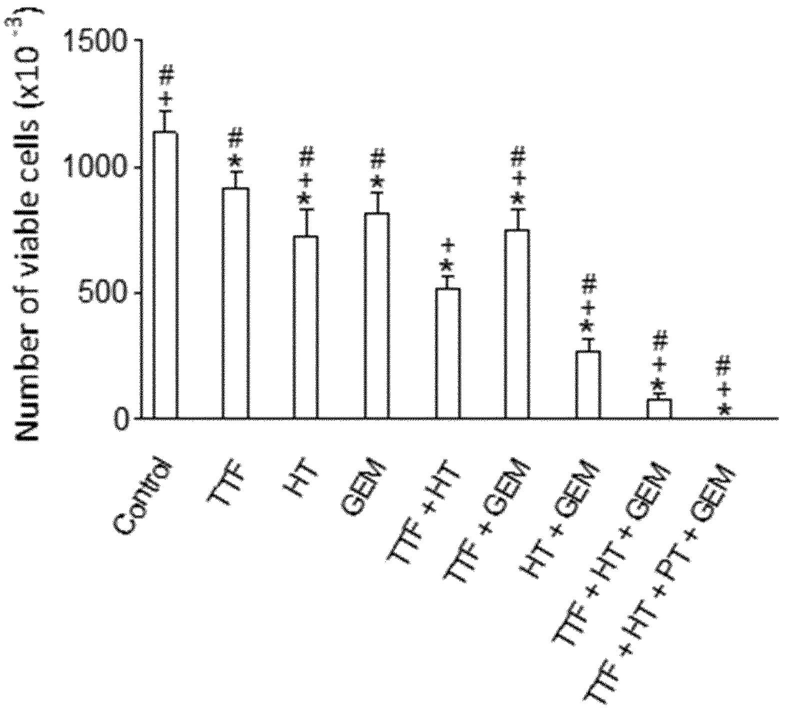
FIG. 22 shows experimental data showing the in vitro effect of TT-Fields ("TTF"), hyperthermia ("HT"), gemcitabine ("GEM"), pterostilbene ("PT") and their combinations on AsPC1 cells.

FIG. 22 shows experimental data showing the in vitro effect of TT-Fields ("TTF"), hyperthermia ("HT"), gemcitabine ("GEM"), pterostilbene ("PT") and their combinations on AsPC1 cells. For TTF data, the TT-Field applied was at 200 kHz for 240 mins (from minute 0 to minute 240) for a field intensity of 1.5 μT. For HT data the hyperthermia applied was 52° C. for 20 minutes (from minute 120 to minute 140). For GEM data 25 μM of gemcitabine was applied from minute 0 to minute 240. For PT data 20 μM of pterostilbene was applied from minute 0 to minute 240. The data shows mean number of viable cells for 5 experiments per experimental condition, with $P<0.01$ using Student's t test vs the control for those labelled *, vs TTF for those labelled + and vs TTF+HT for those labelled #. The application of all four treatments in combination eliminated the AsPC1 cells.

Figure 23:
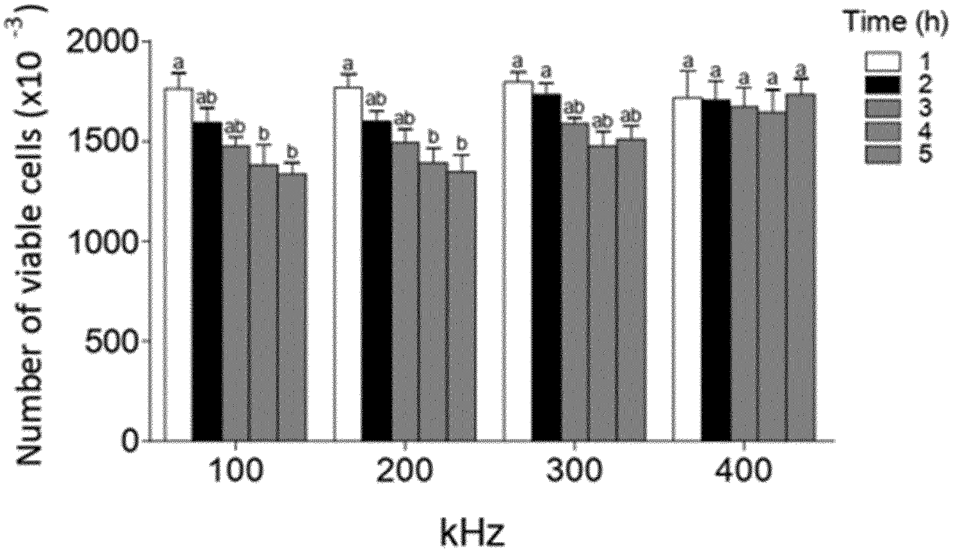
FIG. 23 shows the shows in vitro experimental data for the effect on cell viability for A2058 (melanoma, ATCC) cells when exposed to an oscillating magnetic field.

FIG. 23 shows the shows in vitro experimental data for the effect on cell viability for A2058 (melanoma, ATCC) cells when exposed to different oscillating magnetic fields Different cell cultures were exposed to one of the following magnetic fields: 2 μT at a frequency of 100 kHz; 1.5 μT at a frequency of 200 kHz; 0.7 μT at a frequency of 300 kHz; or 0.5 μT at a frequency of 400 kHz. Cell viability for each frequency after 1, 2, 3, 4 and 5 hours was measured for each cell culture. Five independent experiments were performed for each frequency and time point. The data for each frequency shows the average cell viability and standard deviation over time (1 to 5 hours from left to right) for the 5 corresponding experiments. A two-ways analysis of variance (ANOVA) was used to make comparisons among the different groups. It can be seen that cell viability is reduced for all frequencies, below 300 kHz. Letters "a" and "b" are assigned to the data based on statistical tests applied to the data. Data labelled with the same letter are considered statistically similar, whereas data assigned different letters are considered significantly different with P less than 0.01.

Figure 24:
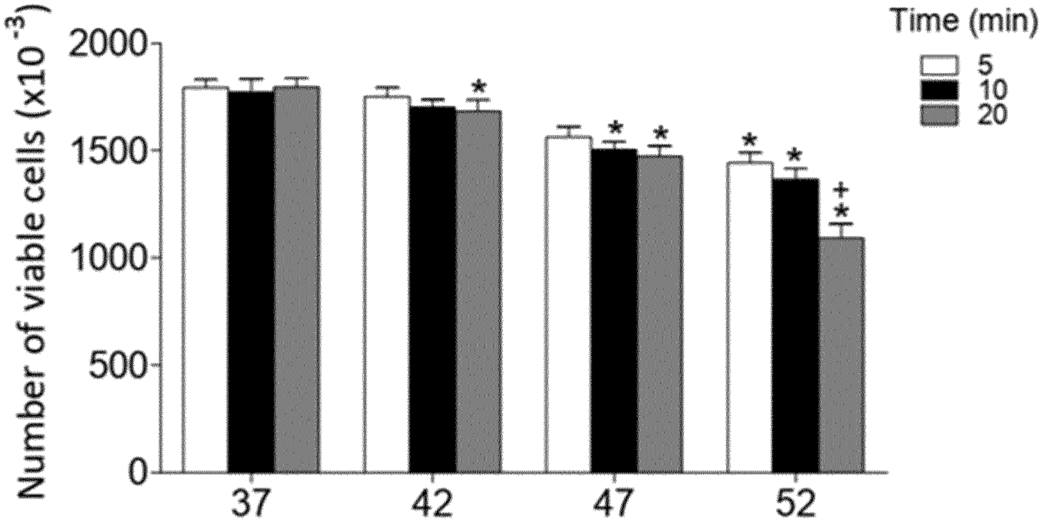
FIG. 24 shows in vitro experimental data for the effect on cell viability for A2058 cells when exposed to heat.

FIG. 24 shows in vitro experimental data for the effect on cell viability for A2058 cells when exposed to heat. Different cell cultures were heated to temperatures of 37, 42, 47 or 52° C. Five independent experiments were performed for each temperature and time point. The data for each temperature shows the average cell viability and standard deviation of the five corresponding experiments after 5, 10 and 20 minutes of exposure to the temperature. Heating to 52° C. reduced the viability of A2058 cells significantly. The data labelled * indicates a P value (student's t test) less than 0.01 compared to the 37° C. data at the corresponding time, and the data labelled + indicates a P value less than 0.01 for the data at 10 and 20 minutes compared to the data at 5 mins for the same temperature.

Figure 25:
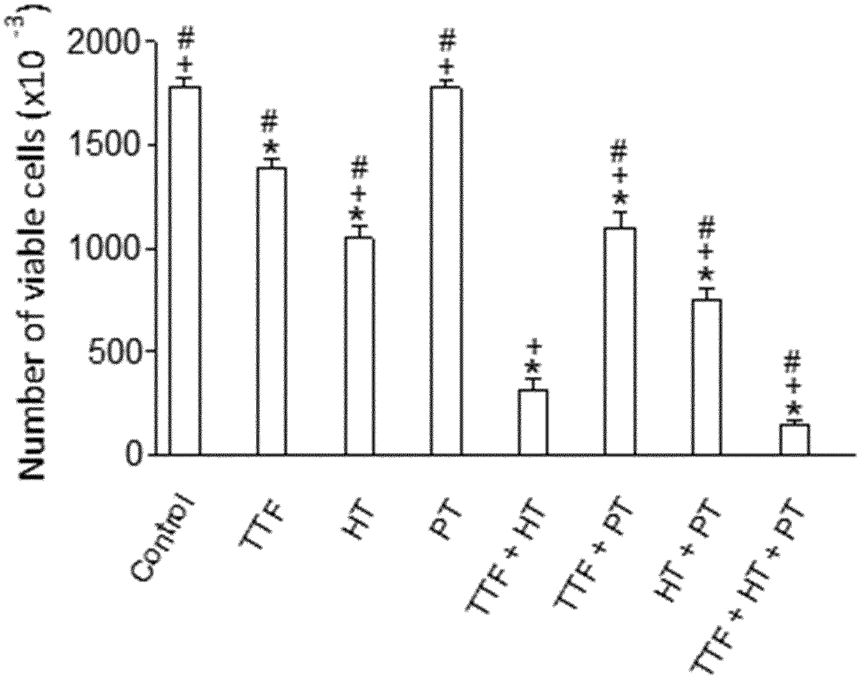
FIG. 25 shows experimental data showing the in vitro effect of TT-Fields ("TTF"), hyperthermia ("HT"), pterostilbene ("PT") and their combinations on A2058 cells.

FIG. 25 shows experimental data showing the in vitro effect of TT-Fields ("TTF"), hyperthermia ("HT"), pterostilbene ("PT") and their combinations on A2058 cells. For TTF data, the TT-Field applied was at 200 kHz for 240 mins (from minute 0 to minute 240) for a field intensity of 1.5 μT. For HT data the hyperthermia applied was 52° C. for 20 minutes (from minute 120 to minute 140). For PT data 20 μM of pterostilbene was applied from minute 0 to minute 240. The data shows mean number of viable cells for 5 experiments per experimental condition, with $P<0.01$ using Student's t test vs the control for those labelled *, vs TTF for those labelled + and vs TTF+HT for those labelled #. The application of all four treatments significantly reduced the viability of the cells compared to TTF+HT.

Comparing the data of FIGS. 12, 20 and 25, the data show that the use of a higher magnetic flux density (about 8 μT or above) allows for heating of the tissue to a lower temperature whilst still maintaining or even improving the effectiveness of the treatment. The combination of such a higher magnetic flux density in combination with heating to temperatures above 42° C. and administration of pterostilbene may be sufficient to eliminate the tumour. This is of special importance to areas of the body to which only limited heating can be applied (for example the brain). The data of, for example, FIG. 22, show that even if a lower magnetic field is used, the cancer cells may be reduced or even eliminated if the tumour treating field and heating is used in combination with one or more of pterostilbene and another anti-cancer drug.

FIGS. 26B to 26H show microscopic images of in vitro A2058 cell cultures after exposed to different external treatments. FIG. 26A shows a microscopic image of a control in vitro AsPC1 cell culture which was not exposed to any external treatments and maintained at the physiological internal temperature of 37° C. FIG. 26B shows a cell culture after being exposed to an electromagnetic field having a magnetic flux density of about 1.5 μT at 200 kHz from 0 to 240 minutes. FIG. 26C shows a cell culture after being exposed to heating to 52° C. for 20 minutes from minute 120 to 140. FIG. 26D shows a cell culture after being exposed to 20 μM pterostilbene from minute 0 to minute 240. FIG. 26E shows a cell culture after exposure to an electromagnetic field having a magnetic flux density of about 1.5 μT at 200 kHz from 0 to 240 minutes and 20 μM pterostilbene from minute 0 to minute 240. FIG. 26F shows a cell culture after exposure to an electromagnetic field having a magnetic flux density of about 1.5 μT at 200 kHz from 0 to 240 minutes and heating to 52° C. for 20 minutes from minute 120 to 140.

FIG. 26G shows a cell culture after exposure to an electromagnetic field having a magnetic flux density of about 1.5 μT at 200 kHz from 0 to 240 minutes, heating to 52° C. for 20 minutes from minute 120 to 140 and 20 μM pterostilbene (PT) from minute 0 to minute 240. FIG. 26H shows the cell culture of FIG. 26G after 24 hours where cultured cells were maintained at 37° C. without any treatment. The growing cells do not seem to recover 24 hours after the combined treatment of FIG. 26G.

Figure 27:
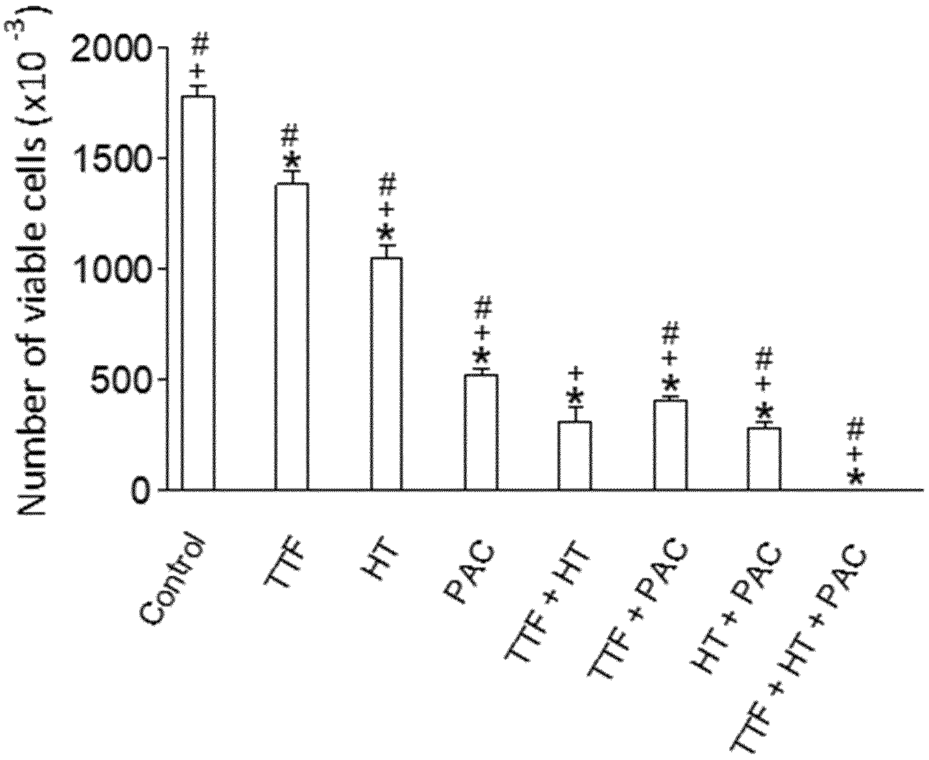
FIG. 27 shows experimental data showing the in vitro effect of TT-Fields ("TTF" and "TTF" are used interchangeably), hyperthermia ("HT"), paclitaxel ("PAC") and their combinations on A2058 cells.

FIG. 27 shows experimental data showing the in vitro effect of TT-Fields ("TTF"), hyperthermia ("HT"), paclitaxel ("PAC") and their combinations on A2058 cells. For TTF data, the TT-Field applied was at 200 kHz for 240 mins (from minute 0 to minute 240) for a field intensity of 1.5 μT. For HT data the hyperthermia applied was 52° C. for 20 minutes (from minute 120 to minute 140). For PAC data 10 μM of paclitaxel was applied from minute 0 to minute 240. The data shows mean number of viable cells for 5 experiments per experimental condition, with P<0.01 using Student's t test vs the control for those labelled *, vs TTF for those labelled + and vs TTF+HT for those labelled #. The application of all three treatments eliminated the cells.

Table 1 shows data examining the effect of GSH depletion on cell viability for U87MG, AsPC1 and A2058 cells in vitro. For rows including "TTF", a TT-Field was applied at 200 kHz for 240 mins (from minute 0 to minute 240) for a field intensity of 1.5 μT. For rows including "HT", hyperthermia applied was at 42° C. for U87MG and 52° C. for AsPC1 and A2058 for 20 minutes (from minute 120 to minute 140). For rows including "BSO", 1 mM of buthione sulfoximine, a specific inhibitor of GSH synthesis, was added to the cell culture medium at the time the cells of the culture were seeded. When HT and TTF were applied in combination with BSO, the HT and TTF were applied 24 hours after seeding. The data show the means and standard deviations for five independent experiments. Data labelled * has a P-value (student's t test) of less than 0.01 compared with the control data. The data labelled + has a P-value (student's t test) of less than 0.01 compared with the TTF+HT data. The data therefor indicate that GSH depletion potentiates the anticancer effect of the electromagnetic radiation and heat.

TABLE 1

| | U87 (GBM) | | AsPC1 (Pancreatic adenocarcinoma) | | A2058 (melanoma) | |
|---|---|---|---|---|---|---|
| | GSH (nmol/$10^6$ cells) | Cell viability (%) | GSH (nmol/$10^6$ cells) | Cell viability (%) | GSH (nmol/$10^6$ cells) | Cell viability (%) |
| Control | 7.15 ± 1.06 | 98.3 ± 1.2 | 15.75 ± 2.7 | 98.9 ± 1.1 | 9.05 ± 1.70 | 98.5 ± 1.1 |
| TTF + HT | 4.02 ± 0.84* | 26.9 ± 5.4* | 6.58 ± 1.12* | 55.4 ± 7.5* | 4.37 ± 1.25* | 28.4 ± 6.4* |
| BSO | 2.10 ± 0.70* | 93.1 ± 1.0* | 3.14 ± 0.79* | 90.1 ± 2.9* | 2.24 ± 0.82* | 91.7 ± 2.8* |
| TTF + HT + BSO | 1.92 ± 0.59*+ | 3.8 ± 2.7*+ | 2.49 ± 0.66*+ | 15.3 ± 3.9*+ | 2.06 ± 0.51*+ | 7.2 ± 2.5*+ |

Accordingly, the use of the apparatuses disclosed herein in combination with the application of pterostilbene provides a highly effective method of treating a cancerous site, and may even entirely eliminate the cancerous cells altogether. Therefore, in one aspect, said anti-carcinogenic composition comprises (i) pterostilbene, pterostilbene phosphate or a pharmaceutically acceptable salt thereof. Alternatively, the anti-cancer composition may be provided in a cocrystal, a water-soluble prodrug, nanoparticle, nanodot, nanorob, nanospike, nanorod, nanocluster, nanoceramic, liposome or exosome formulation, or may be provided in an implantable device configured to release the anti-cancer composition when implanted in the body. Please note that said anti-carcinogenic composition may comprise any anti-oxidant composition. In this sense, the anti-carcinogenic composition may comprise any stilbenoid, apart from pterostilbene, suitable as an anti-carcinogenic agent, such as resveratrol.

(i) Pterostilbene and Pterostilbene Phosphate

The term "pterostilbene" or "Pter" or "trans-3,5-dimethoxy-4'-hydroxystilbene" as used herein, refers to a compound of formula

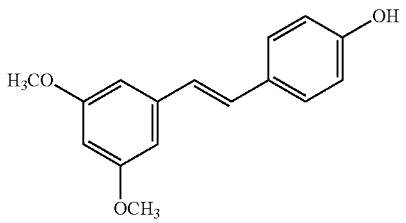 [SMILES: COc1cc(/C=C/c2ccc(O)cc2)cc(OC)c1]

The term "pterostilbene phosphate" refers to a compound of formula

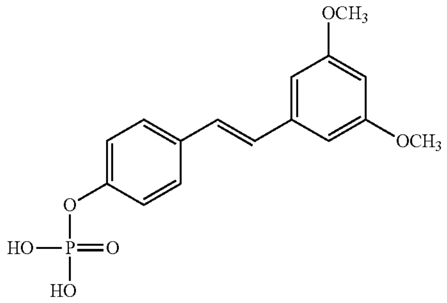 [SMILES: COc1cc(/C=C/c2ccc(OP(=O)(O)O)cc2)cc(OC)c1]

The term "pharmaceutically acceptable salt" refers to any salt of pterostilbene or pterostilbene phosphate which, upon administration to the recipient is capable of providing (directly or indirectly) a compound as described herein. Preferably, as used herein, the term "pharmaceutically acceptable salt" means approved by a regulatory agency of the Federal or a state government or listed in the U.S. Pharmacopeia or other generally recognized pharmacopeia for use in animals, and more particularly in humans. The preparation of salts can be carried out by methods known in the art. Illustrative non-limitative examples of pharmaceutically acceptable salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate salts. The pharmaceutically acceptable salts of pterostilbene or pterostilbene phosphate are preferably prepared from a polyphenol compound having an acidic functional group, and an acceptable inorganic or organic base. Suitable bases include, but are not limited to, hydroxides of alkali metals such as sodium, potassium, and lithium; hydroxides of alkaline earth metals such as calcium and magnesium; hydroxides of other metals, such as aluminum and zinc; ammonia, and organic amines, such as unsubstituted or hydroxy-substituted mono-, di-, ortri-alkylamines, dicyclohexylamine; tributyl amine; pyridine; N-methyl, N-ethylamine; diethylamine; triethylamine; mono-, bis-, or tris-(2-hydroxy substituted lower alkylamines), such as mono-; bis-, or tris-(2-hydroxyethyl) amine, 2-hydroxy-tert-butylamine, or tris-(hydroxymethyl) methylamine, N,N-di-lower alkyi-N-(hydroxy lower alkyl)-amines, such as N,N-dimethyl-N-(2-hydroxyethyl)amine or tri-(2-hydroxyethyl)amine; N-methyl-0-glucamine; and amino acids such as arginine, lysine, and the like. The term "pharmaceutically acceptable salt" also includes a hydrate of a polyphenol compound. In a particular embodiment, the pharmaceutically acceptable salt is a disodium salt.

Further illustrative non-limitative examples of cancer chemotherapeutic agents which may be in accordance to the present invention include: alkylating agents such as nitrogen mustards/oxazaphosphorines (e.g. cyclophosphamide, ifosfamide), nitrosoureas (e.g. carmustine), triazenes (e.g. temozolamide), and alkyl sulfonates (e.g. busulfan); antimetabolite drugs (for example 5-fluorouracil, capecitabine, 6-mercaptopurine, methotrexate, gemcitabine, cytarabine, fludarabine or pemetrexed); anthracycline antibiotics such as doxorubicin and daunorubicin, taxans such as Taxol™ and docetaxel, vinca alkaloids such as vincristin and vinblastine, 5-fluorouracil (5-FU), leucovorin, irinotecan, idarubicin, mitomycin C, oxaliplatin, raltitrexed, pemetrexed, tamoxifen, cisplatin, carboplatin, methotrexate, actinomycin D, mitoxantrone, blenoxane, mithramycin, paclitaxel, 2-methoxyestradiol, prinomastat, batimastat, BAY 12-9566, carboxyamidotriazole, CC-1088, dextromethorphan acetic acid, dimethylxanthenone acetic acid, endostatin, IM-862, marimastat, penicillamine, PTK787/ZK 222584, RPI.4610, squalamine lactate, SU5416, thalidomide, combretastatin, COL-3, neovastat, BMS-275291, SU6668, anti-VEGF antibodies, Medi-522 (Vitaxin II), CAI, Interleukin 12, IM862, amiloride, angiostatin, angiostatin K1-3, angiostatin K1-5, captopril, DL-alpha-difluoromethylornithine, DL-alpha-difluoromethylornithine HC1, endostatin, fumagillin, herbimycin A, 4-hydroxyphenylretinamide, juglone, laminin, laminin hexapeptide, laminin pentapeptide, lavendustin A, medroxyprogesterone, minocycline, placental ribonuclease inhibitor, suramin, thrombospondin, antibodies targeted against proangiogenic factors (for example, bevacizumab, cetuximab, panitumumab, trastuzumab); topoisomerase inhibitors; antimicrotubule agents; low molecular weight tyrosine kinases inhibitors of proangiogenic growth factors (for example erlotinib, sorafenib, sunitinib, gefitinib); GTPase inhibitors; histone deacetylase inhibitors; AKT kinase or ATPase inhibitors; Wnt signaling inhibitors; inhibitors of the E2F transcription factor; mTOR inhibitors (for example temsirolimus); alpha, beta and gamma interferon, IL-12, matrix metalloproteinase inhibitors (for example, COL3, Marimastat, Batimastat); ZD6474, SU11248, vitaxin; PDGFR inhibitors (for example imatinib); NM3 and 2-ME2; cyclic peptides such as cilengitide. Other chemotherapy agents suitable are described in detail in The Merck Index in CD-ROM, 13rd Edition. In a preferred embodiment of the invention, chemotherapeutic agents are selected from the group consisting of docetaxel (Taxotere®), cisplatin, pemetrexed, gemcitabine and irinotecan.

In a particular embodiment, the cancer chemotherapeutic agent is a taxane, preferably which comprises or consists on paclitaxel. The term "paclitaxel", as used herein, refers to a compound with chemical name (2α,4α,5β,7β,10β,13α)-4,10-Bis(acetyloxy)-13-{[(2R,3 S)-3 (benzoylamino)-2-hydroxy-3-phenylpropanoyl]oxy}-1,7-dihydroxy-9-oxo-5,20-epoxytax-11-en-2-yl benzoate and having the chemical formula

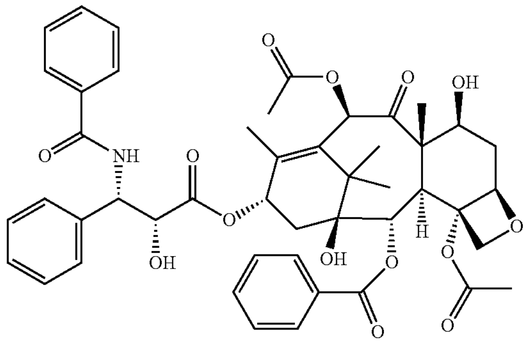 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

In a more particular embodiment, the paclitaxel is protein bound paclitaxel. The term "protein-bound paclitaxel" or "nab-paclitaxel" or "nanoparticle albumin-bound paclitaxel", as used herein, refers to a formulation in which paclitaxel is bound to albumin as a delivery vehicle.

The cancer chemotherapeutic agent will vary depending on the type of cancer that is going to be treated with the combination of the invention. The skilled person can easily determine which cancer chemotherapeutic agent is more suitable to treat a particular type of cancer.

Also optionally, in step S4, a Glutathione (GSH) depleting agent is provided to the target site in addition to the anti-carcinogenic compound. The GSH depleting agent may be administered by any suitable means, such as orally or intravenously. It is noted that the GSH depleting agent may be provided before or simultaneously to steps S1, S2 and step S3 or a predetermined time after step S1, S2 or S3, preferably at a predetermined time after step S3. The GSH depleting agent provided may be any GSH depleting agent disclosed herein, including in relation to FIGS. 12 to 27 or Table 1.

The term "glutathione depleting agent", as used herein, refers to a substance that reduces or eliminates glutathione from a cell that has been contacted with that substance. The skilled person is able of determining if a particular molecule is a glutathione depleting agent, for example, by comparing the effect of the particular molecule with the effect of buthionine sulfoximine (BSO), a specific inhibitor of gamma-glutamyl-cysteinyl ligase, using the methodology described for in vitro and in vivo conditions by Terradez P et al, Biochem J 1993, 292 (Pt 2): 477-83. In a particular embodiment, a particular molecule is a glutathione depleting agent if said molecule has at least a 10%, at least a 20%, at least a 30%, at least a 40%, at least a 50%, at least a 60%, at least a 70%, at least a 80%, at least a 90%, a 100% or more of the glutathione-depleting effect of buthionine sulfoximine. Illustrative non-limitative examples of glutathione depleting agents are:

a) A Bcl-2 antisense oligodeoxynucleotide, that is, an oligodeoxynucleotide which is complementary to the RNA sequence of the Bcl-2 gene, as described by Ortega, et al., *Cancers* (*Basel*) 2011, 3, 1285-1310. Non-limitative examples of Bcl-2 antisense oligodeoxynucleotides are described in U.S. Pat. No. 5,734,033, WO2003040182A1, U.S. Pat. No. 5,831,066A. Assays for determining if a particular compound is a Bcl-2 antisense oligodeoxynucleotide are, for example, those based on the effect of a compound on the mRNA levels of Bcl-2 or on the Bcl-2 protein levels, as described by Mena et al., Clinical Cancer Research 2007, 13 (9): 2658-66.

b) An inhibitor of multidrug resistance protein 1 (MRP1). As described by Ortega, et al., supra.

The term “MRP1 inhibitor”, as used herein, refers to a compound inhibiting the activity of the MRP1. The term inhibitor includes, without limitation, antagonists of MRP1, antibodies against MRP1, compounds which prevent expression of MRP1 and compounds which lead to reduced mRNA or protein levels of the MRP1. Non-limitative examples of an inhibitor of MRP1 are verapamil and MK-571. An assay for determining if a particular compound is a MRP1 inhibitor is, for example, the methodology described in Olson D. P. et al., Cytometry 2001, 46 (2): 105-13.

c) An inhibitor of the gamma-glutamyl transpeptidase or gamma glutamyl transferase (GGTP or GGT), like those described by Silber et al., Anal Biochem 1986, 158 (1): 68-71.

The term “GGTP inhibitor”, as used herein, refers to a compound inhibiting the activity of the GGTP, which is an enzyme which catalyzes the transfer of the gamma-glutamyl moiety of glutathione to an acceptor. The term inhibitor includes, without limitation, antagonists of GGTP, antibodies against GGTP, compounds which prevent expression of GGTP and compounds which lead to reduced mRNA or protein levels of the GGTP. GGTP inhibitors include both selective and non-selective (also affecting asparagine synthetase) inhibitors. Non-limitative examples of an inhibitor of GGTP are acividin and 2-amino-4-{[3-(carb oxymethyl)phenyl](methyl) phosphono}butanoic acid (GGsTop™). Assays for determining if a particular compound is a GGTP inhibitor are, for example those described by Silver et al., Anal Biochem 1986, 158 (1): 68-71.

d) An inhibitor of cystine uptake, as described by Obrador, et al., Hepatology 2002, 35, 74-81.

The term “inhibitor of cystine uptake” refers to a compound inhibiting any of the systems by which extracellular cystine is transported inside the cell, including the sodium-independent $X_c^-$ system and the sodium-dependent XAG system (McBean G. J. and Flynn J., Biochem Soc Trans. 2001, 29 (Pt6): 712-22). The term inhibitor includes both competitive and non-competitive inhibitors. Non-limitative examples of inhibitors of cystine uptake are acivicin, L-glutamate, L-serine-o-sulphate, L-cysteine sulphinate, L-cysteine, L-trans-pyrrolidine-2,4-dicarboxylate and kainite. Assays for determining if a particular compound is an inhibitor of cysteine uptake are, for example, assays based on the determination of the uptake of $^{35}$S-labeled cysteine.

e) Glutathione disulfide (NOV-002), a compound having the formula

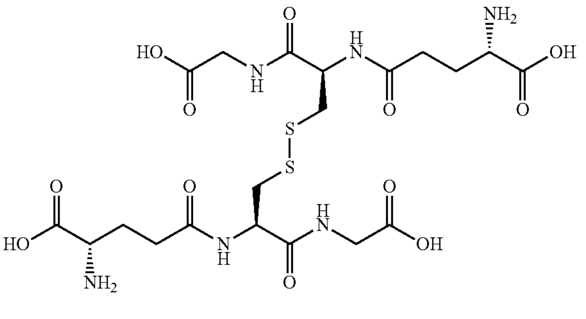 [SMILES: N[C@@H](CCC(=O)N[C@@H](CSSC[C@H](NC(=O)CC[C@H](N)C(=O)O)C(=O)NCC(=O)O)C(=O)NCC(=O)O)C(=O)O]

or its disodium salt disodium glutathione disulfide, as described by Gumireddy et al., *J Carcinog Mutagen* 2013 (2013).

f) Phenethyl isothiocyanate, a compound having the formula

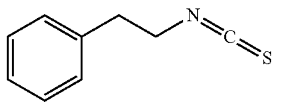 [SMILES: S=C=NCCc1ccccc1]

as described by Trachootham, et al., *Cancer Cell* 2006, 10: 241-252.

g) A glucocorticoid receptor antagonist, as described by Min, et al., *J Mol Med* (Berl) 2012, 90: 309-319.

The term “glucocorticoid receptor antagonist” refers to a compound that binds a glucocorticoid receptor and lacks any substantial ability to activate the receptor itself. The term “glucocorticoid receptor antagonist” includes both neutral antagonists and inverse antagonists. A “neutral antagonist” is a compound that blocks the action of the agonist but has no effect on intrinsic or spontaneous receptor activity. An “inverse antagonist” is able to both block the action of the agonist at the receptor and attenuate the constitutive activity of the receptor. The term “antagonist” also includes competitive antagonists, which are drugs that bind to the same site as the natural ligand; noncompetitive antagonists which bind to a different site on the receptor than the natural ligand; reversible antagonists which bind and unbind the receptor at rates determined by receptor-ligand kinetics; and irreversible antagonists which bind permanently to the receptor either by forming a covalent bond to the active site or just by binding so tightly that the rate of dissociation is effectively zero. Non-limitative examples of glucocorticoid receptor antagonists are RU-486 (mifepristone), RU-43044, octahydrophenanthrenes, spirocyclic dihydropyridines, triphenylmethanes and diaryl ethers, chromenes, dibenzyl anilines, dihydroisoquinolines, pyrimidinediones, azadecalins, aryl pyrazolo azadecalins, 11-monoaryl steroids, phenanthrenes, dibenzol [2.2.2]cycloctanes and derivatives, dibenzoclycloheptanes and their derivatives, dibenzyl anilinesulfonamides and their derivatives, dihetero (aryl) pentanol, chromene derivatives, azadecalins, aryl quinolones, 11,21-bisaryl steroids and 11-aryl, and 16-hydroxy steroids and the dual antagonist-agonists beclomethasone, betamethasone, budesonide, ciclesonide, flunisolide, fluticasone, mometasone, and triamcinolone. Whether a particular compound is a glucocorticoid receptor antagonist can be determined, for example, by commercial kits, like the Glucocorticoid receptor pathway reporter kit (BPS BIOSCIENCE, SAN DIEGO, CA, USA)

h) An anti-IL-6 agent, as described by Obrador et al. *J Blot Chem* 2011, 286: 15716-15727. The term "anti-IL-6 agent" refers to a compound which is capable of decreasing the activity of IL-6 either by diminishing its levels, by totally or partially blocking the binding to its receptor or by totally or partially inhibiting its receptor activity. The term "anti-IL-6 agent" includes inhibitory antibodies against IL-6, i.e., antibodies that bind to IL-6 preventing IL-6 to bind to its receptor, like for example elsilimomab and siltuximab, and inhibitors of IL-6 receptor, like tocilizumab. Assays for determining if a particular compound is an anti-IL6 agent are, for example, an ELISA for determining IL6 levels, like the kit of Life Technologies, Carlsbad, CA, USA, or an assay for determining the intracellular signaling derived from the binding of IL6 to its receptor, like the IL6/STAT3 Signaling Pathway Plus PCR Array de Quiagen (Valencia, CA, USA).

i) Buthionine sulfoximine (BSO), which is a compound having the formula

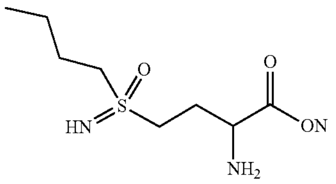

The glutathione depleting effect of BSO has been described by Terradez P. et al., Biochem J. 1993, 292: 477-483.

j) Diethylmaleate or DEM, which is a compound having the formula

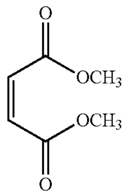

The glutathione depleting effect of DEM has been described by Estrela J. M. et al., Nat Med 1995, 1(1): 84-88.

k) NPD926, a compound having the formula

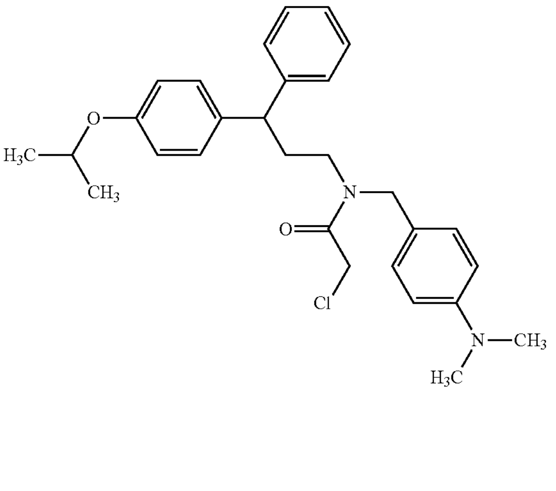 [SMILES: CC(C)Oc1ccc(C(CCN(Cc2ccc(N(C)C)cc2)C(=O)CCl)c2ccccc2)cc1]

The glutathione depleting effect of NPD926 has been described by Kawamura T et al., Biochem J 2014, 463: 53-63.

l) Parthenolide, a compound having the formula

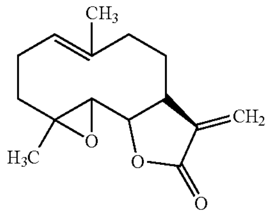

The glutathione depleting effect of parthenolide has been described by Pei S. et al., J Biol Chem 2013, 288 (47): 33542-58.

m) A compounds having the formula

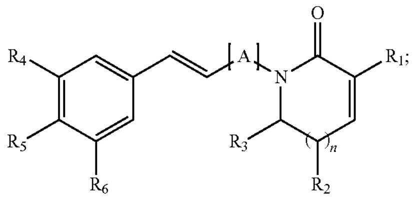

wherein A is C(O) or S(O)2; wherein n=0, 1, 2, or 3; wherein the ortho-carbon of the phenyl ring is unsubstituted or substituted with a halogen; wherein R1 is selected from the group consisting of hydrogen, halogen, C≡C-alkyl, C≡C-cycloalkyl, C≡C-cycloakyl halide, C≡C-aryl, C≡C-aryl halide, and an aryl group; wherein R2 is selected from the group consisting of hydrogen, alkyl, alkenyl, and an aryl group; wherein R3 is selected from the group consisting of hydrogen, alkyl, alkenyl, and an aryl group; and, wherein each of R4, R5, and R6 is independently selected from the group consisting of hydrogen, bromine, chlorine, fluorine, keto, hydroxyl, alkyl, alkenyl, alkoxy, methoxy, aminoalkyl, aminoalkenyl, and an aminoalkoxy group.

In particular, Piperlongumine, a compound having the formula

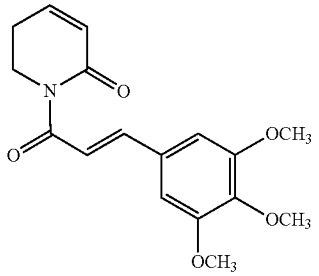 [SMILES: COc1cc(/C=C/C(=O)N2CCC=CC2=O)cc(OC)c1OC]

The glutathione depleting effect of piperlongumine has been described by Pei S. et al., supra.

n) An inhibitor of a protein from the bromodomain and extraterminal domain family as described by Shao Q. et al., Cancer Research 2014, 74 (23):7090-102.

The term “inhibitor of a protein from the bromodomain and extraterminal (BET) domain family” or “BET inhibitor” refers to a compound which binds the bromodomain of bromodomain and extraterminal (BET) proteins BRD2 BRD3, BRD4 and BRDT preventing protein-protein interaction between BET proteins and acetylated histones and transcription factors. The term “BET inhibitor” includes inhibitors targeting any of BRD2, BRD3, BRD4 and BRDT. Non-limitative examples of BET inhibitors are JQ1, GSK525762A and OTX-015. Assays for determining if a particular compound is a BET inhibitor are, for example, the Homogeneous Proximity Assay from BioTek (Winooski, VT, USA) for screening inhibitors of BRD4.

In a particular embodiment, the glutathione depleting agent of the combination of the invention is selected from the group consisting of: a) a Bcl-2 antisense oligodeoxynucleotide; b) an inhibitor of multidrug resistance protein 1; c) an inhibitor of the gamma-glutamyl transpeptidase; d) an inhibitor of cystine uptake; e) disodium glutathione disulfide; f) phenethyl isothiocyanate; g) a glucocorticoid receptor antagonist; h) an anti-IL-6 agent; i) buthionine sulfoximine; j) diethylmaleate; k) NPD926; 1) parthenolide; m) piperlongumine and n) an inhibitor of a protein from the bromodomain and extraterminal domain family, in particular GSK525762A or I-BET762.

In a more particular embodiment the inhibitor of multidrug resistance protein 1 is verapamil, which is a compound having the formula

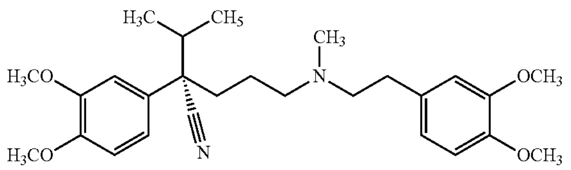

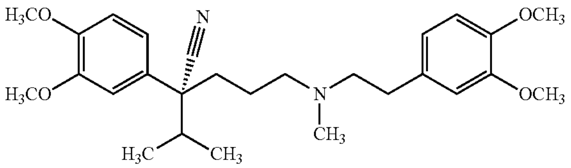

In a more particular embodiment, the inhibitor of gamma-glutamil transpeptidase is acivicin, which is a compound having the formula

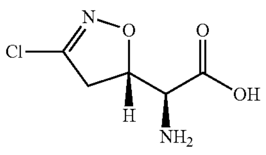 [SMILES: N[C@H](C(=O)O)[C@@H]1CC(Cl)=NO1]

In a more particular embodiment, the inhibitor of cystine uptake is sulfasalazine, which is a compound having the formula

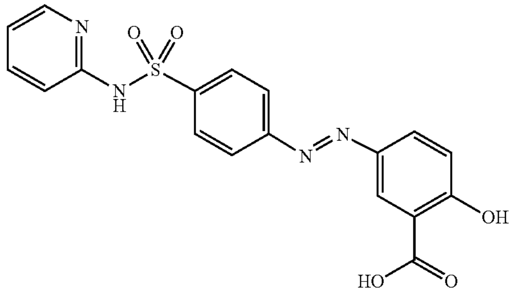 [SMILES: O=C(O)c1cc(/N=N/c2ccc(S(=O)(=O)Nc3ccccn3)cc2)ccc1O]

In a more particular embodiment, the glucocorticoid receptor antagonist is RU-486 or mifepristone, which is a compound having the formula

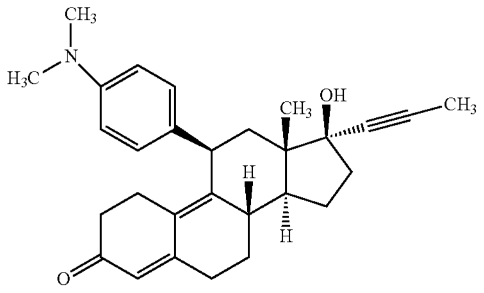

In a more particular embodiment, the anti-IL-6 agent is an inhibitory antibody against IL-6 or an inhibitor of the IL-6 receptor. In an even more particular embodiment, the anti-IL-6 agent is selected from the group consisting of tocilizumab, elsilimomab and siltuximab. The term “tocilizumab” refers to a humanized monoclonal antibody against the IL-6 receptor. The term “elsilimomab” refers to a mouse monoclonal antibody against IL-6. The term “siltuximab” or “CNTO 328” refers to a chimeric monoclonal antibody against IL-6.

In a more particular embodiment, the inhibitor of a protein from the bromodomain and extraterminal domain family is selected from the group consisting of JQ1, GSK525762A and OTX-015. The term “JQ1” refers to a compound of formula

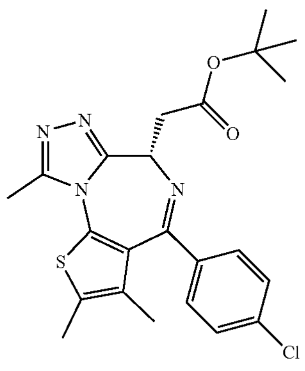 [SMILES: Cc1sc2c(c1C)C(c1ccc(Cl)cc1)=N[C@@H](CC(=O)OC(C)(C)C)c1nnc(C)n1-2]

The term “GSK525762A” refers to a compound of formula

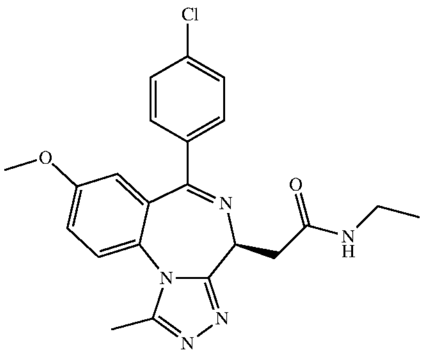 [SMILES: CCNC(=O)C[C@@H]1N=C(c2ccc(Cl)cc2)c2cc(OC)ccc2-n2c(C)nnc21]

The term "OTX-015" refers to a compound of formula

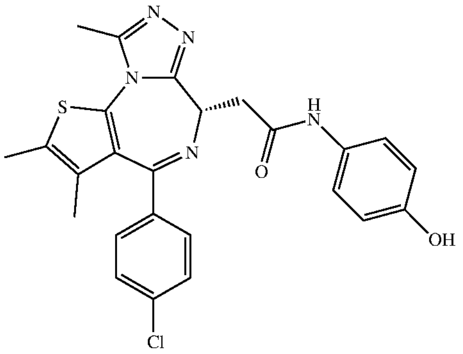 [SMILES: Cc1sc2c(c1C)C(c1ccc(Cl)cc1)=N[C@@H](CC(=O)Nc1ccc(O)cc1)c1nnc(C)n1-2]

The term "CPI-0610" refers to the compound of reference CAT #: 206117 markered by MedKoo Biosciencies Inc.

In a particular embodiment, the glutathione depleting agent is diethylmaleate, GSK525762A (I-BET762) or piperlongumine.

In step S5, the direct heating is stopped and in step S6 the non-ionizing alternating electric field is stopped. It is noted that steps S5 and S6 may occur simultaneously or the direct heating may be stopped before the non-ionizing alternating electromagnetic field is stopped, such that only the non-ionizing alternating electromagnetic field is applied for a predetermined time after the direct heating is stopped.

It is noted that the order in which the steps are presented in FIG. 11 does not require any chronological order on steps S1 to S5. For example, steps S3 and/or S4 (depending on whether either or both are implemented in the method) may be implemented at the same time as the start of step S1, or a predetermined time after step S1 begins but before step S2 begins, or at the same time as the start of step S2, or a predetermined amount of time after the start of step S2. Further, in examples where both S3 and S4 are implemented, they may be implemented at the same or different times. For example, independently of when (or whether) step S4 is implemented, step S3 may be implemented at the same time as the start of step S1, or a predetermined time period after the start of step S1 but before the start of step S2, or at the same time as the start of step S2, or a predetermined time after the start of step S2. Meanwhile, independently of when (or whether) step S3 is implemented, step S4 may be implemented at the same time as the start of step S1, or a predetermined time after the start of step S1 but before the start of step S2, or at the same time as the start of step S2 or a predetermined time after the start of step S2. Further, step S1 may be applied for a first time period and step S2 may be applied for a second time period, and the second time period may partially or completely overlap with the first time period or the second time period may begin when the first time period expires.

For example, the non-ionizing alternating electromagnetic field (e.g. at 300 kHz) may be provided at the same time as the anti-cancer composition and the GSH depletor (for example pterostilbene and gemcitabine). The alternating electromagnetic field is applied for two hours, and heating is applied within this two-hour period (for example to heat the target site to a temperature of 52° C. for 10 minutes). In another example, non-ionizing alternating electromagnetic field may be provided first (e.g. at 300 kHz) for a first time period (e.g. 2 hours), and upon expiry of the first time period heating is applied in combination with the anti-cancer composition and/or the GSH depletor (for example pterostilbene with heating to 47° C. for two hours).

In the method, the non-ionizing alternating electromagnetic field may have a frequency of between 10 kHz to 500 kHz, providing a magnetic flux density between 0.1 pT and 1 mT, or between 0.1 pT and 100 μT, or between 100 μT, and 1 mT, and/or the corresponding electric field strength amplitude of between 1 V/cm and 3 V/cm depending on the tissue impedance and may be applied for a time period of between 1 minute and 24 hours.

The direct heating preferably heats the target site to a temperature of at least 42° C., and preferably between 42° C. and 57° C.

Heating of the Target Site by the Tumour Treating Field

The mechanism by which the oscillating magnetic field of the tumour treating field may cause heating of the tissue is through inducing Foucault currents (or "eddy currents") in the tissue. These currents revolve around the magnetic field lines in the tissue and by the Joule effect could heat the tumour cells. This is due to the conductivity, σ, of the living tissue. The conductivity of tumour tissue increases with increasing frequency of the oscillating magnetic field and is approximately 0.15 siemens/metre at 300 kHz. This conductivity provides the path for microscopic eddy currents which flow in circular paths. The power per unit mass, P, that heats these cells is given by the following equation:

$$P=\pi^2B^2d^2f^2/(6\cdot\rho\cdot D)$$

Where B is the magnetic flux density, d is the depth of tissue over which the magnetic field is provided, f is the field frequency, ρ is the tissue resistivity (inverse to the electrical conductivity) and D is the mass density of the tissue.

The conductivity of tumour tissue can be up to five times higher than the conductivity of healthy tissue and has an approximate value of 0.15 siemens/metre at 100-300 kHz. D for biological tissue is variable (between 900-1050 kg/m$^3$), but can be approximated by that of water, 1000 kg/m$^3$. The highest magnetic flux density of the tumour treating field is 1 mT. The highest frequency is 300 kHz. In the in vitro experiments, the thickness of the culture flask was approximately 1 mm which is the value of d. This gives a value for P of 20 pW/kg. This is an extremely low value. The mechanism of the TT-field is therefore not due to heating. Cell death may be the consequence of charge disruption in the mitochondria. This effect is stronger in tumour tissues due to its higher conductivity, approximately five times higher than the conductivity of healthy cells. The synergetic effect with hyperthermia could be attributable to an increase of the conductivity associated with an increase in the mobility of the charged molecules.

All of the above are fully within the scope of the present disclosure and are considered to form the basis for alternative embodiments in which one or more combinations of the above described features are applied, without limitation to the specific combination disclosed above.

In light of this, there will be many alternatives which implement the teaching of the present disclosure. It is expected that one skilled in the art will be able to modify and adapt the above disclosure to suit its own circumstances and requirements within the scope of the present disclosure, while retaining some or all technical effects of the same, either disclosed or derivable from the above, in light of his common general knowledge in this art. All such equivalents, modifications or adaptations fall within the scope of the present disclosure.

The invention claimed is:

1. An apparatus for treating a cancerous target site, comprising:

an electromagnetic emitter comprising one or more electrodes with an electrically insulating coating for preventing electrical contact between the electrodes and the target site, the electromagnetic emitter configured to provide a tumour treating field at a target site via the one or more electrodes, the tumour treating field being a non-ionizing alternating electromagnetic field having a frequency of between 10 kHz to 300 kHz; and further having a magnetic flux density of between 0.1 pT and 1 mT;

a heat source configured to provide heating at the target site to cause hyperthermia at the target site; and an electronic controller for electronically controlling the electromagnetic emitter and the heat source;

wherein the apparatus is configured to apply the non-ionizing alternating electromagnetic field and the heating independently.

2. The apparatus of claim 1, wherein the apparatus is configured to provide the non-ionizing alternating electromagnetic field at the target for a first time period, and to provide the heating at the target site for a second time period.

3. The apparatus of claim 1, wherein the apparatus is configured to provide the non-ionizing alternating electromagnetic field at the target site for a first time period of between 1 minute and 24 hours.

4. The apparatus of claim 1, wherein the apparatus is further configured to provide the heating at the target site for a second time period of between 1 minute and 360 minutes.

5. The apparatus of claim 1, wherein the electromagnetic emitter is configured to provide an alternating electromagnetic field at the target site having a magnetic flux density of between 0.1 pT and 100 μT.

6. The apparatus according to claim 1, wherein the electromagnetic emitter is configured to provide an alternating electromagnetic field at the target site having a magnetic flux density of between 0.5 μT and 1 mT.

7. The apparatus according to claim 1, wherein the electromagnetic emitter is configured to provide an alternating electromagnetic field at the target site having a magnetic flux density of between 8 μT and 1 mT.

8. The apparatus of claim 1, wherein electromagnetic emitter is configured to provide an alternating electromagnetic field having a frequency of between 100 kHz to 300 kHz.

9. The apparatus of claim 1, wherein the heat source is configured to heat the target site to a temperature of above 42° C. and preferably between 42° C. and 57° C.

10. The apparatus of claim 1, wherein the heat source comprises an ultrasonic emitter configured to provide ultrasound radiation to the target site.

11. The apparatus of claim 1, wherein the heat source comprises an electromagnetic emitter configured to provide electromagnetic radiation to the target site.

12. The apparatus of claim 1, wherein the heat source comprises a fluidic pump configured to pump fluid to the target site and a heater to heat the fluid before it reaches the target site.

13. The apparatus of claim 1, wherein the heat source comprises a conductive heat emitter configured to provide heat to the target site by conduction of heat.

14. The apparatus of claim 4, wherein the heating is applied simultaneously to the non-ionizing alternating electromagnetic field for a third time period.

15. The apparatus of claim 9, wherein the heat source is configured to heat the target site to a temperature of between 42° C. and 57° C.

16. The apparatus of claim 10, wherein the ultrasound radiation has one or more focal areas in the target site.

* * * * *